United States Patent
Forsell

(10) Patent No.: US 8,961,464 B2
(45) Date of Patent: Feb. 24, 2015

(54) INFUSION OF DRUGS

(76) Inventor: Peter Forsell, Bouveret (CH)

( * ) Notice: Subject to any disclaimer, the term of this patent is extended or adjusted under 35 U.S.C. 154(b) by 563 days.

(21) Appl. No.: 13/123,227

(22) PCT Filed: Oct. 9, 2009

(86) PCT No.: PCT/EP2009/007285
§ 371 (c)(1),
(2), (4) Date: Apr. 7, 2011

(87) PCT Pub. No.: WO2010/040552
PCT Pub. Date: Apr. 15, 2010

(65) Prior Publication Data
US 2011/0230836 A1    Sep. 22, 2011

Related U.S. Application Data

(60) Provisional application No. 61/136,876, filed on Oct. 10, 2008.

(51) Int. Cl.
*A61M 1/00* (2006.01)
*A61F 2/26* (2006.01)
(Continued)

(52) U.S. Cl.
CPC .............. *A61F 2/26* (2013.01); *A61M 5/14276* (2013.01); *A61M 5/1428* (2013.01);
(Continued)

(58) Field of Classification Search
CPC ..................... A61M 39/0208; A61M 5/14276; A61M 39/0247; A61M 2005/1581; A61M 5/158; A61M 5/14244; A61M 5/14566; A61M 5/16827; A61M 5/172; A61M 5/1689; A61M 5/142; A61M 5/14546

USPC ............ 604/82, 150, 151, 93.01, 65–67, 131; 128/DIG. 1, DIG. 12, DIG. 13
See application file for complete search history.

(56) References Cited

U.S. PATENT DOCUMENTS 4,766,889 A * 8/1988 Trick et al. ...................... 600/40
5,518,499 A   5/1996 Agar
(Continued)

FOREIGN PATENT DOCUMENTS

EP    1 884 259    2/2008
FR    2621248    4/1989
(Continued)

OTHER PUBLICATIONS

International Search Report for PCT/EP2009/007285, mailed Mar. 3, 2010.
(Continued)

*Primary Examiner* — Manuel Mendez

(57) ABSTRACT

A penis erection stimulation system comprises one or more infusion needles, the tip ends of which are disposed within and implanted along with at least one first housing adjacent the patient's left and right corpora cavernosa. The respective other end or ends of the infusion needles are disposed and implanted along with at least one second housing remote from the first housing. A reservoir and a pump are also implanted inside the patient's body to supply the infusion needle with infusion liquid. A drive unit also adapted for implantation inside the patient's body is arranged for advancing and retracting the infusion needle such that its tip end penetrates the at least one first housing's outer wall at least in two different penetration areas either simultaneously or in immediate time succession, thereby injecting drugs into the patient's body for stimulating penis erection.

27 Claims, 24 Drawing Sheets

(51) Int. Cl.
*A61M 5/142* (2006.01)
*A61M 5/145* (2006.01)
*A61M 5/168* (2006.01)

(52) U.S. Cl.
CPC ....... *A61M 5/14593* (2013.01); *A61M 5/16827* (2013.01); *A61M 2005/14284* (2013.01); *A61M 2205/3606* (2013.01); *A61M 2205/3673* (2013.01); *A61M 2205/8243* (2013.01); *A61M 2210/167* (2013.01)
USPC ........................................................ 604/151

(56) References Cited

U.S. PATENT DOCUMENTS

| | | | |
|---|---|---|---|
| 7,660,631 B2 * | 2/2010 | Whitehurst et al. | 607/39 |
| 7,818,062 B2 * | 10/2010 | Gross | 607/39 |
| 2006/0184119 A1 * | 8/2006 | Remde et al. | 604/151 |
| 2008/0015494 A1 * | 1/2008 | Santini et al. | 604/65 |
| 2009/0270811 A1 * | 10/2009 | Mounce et al. | 604/151 |
| 2011/0196198 A1 | 8/2011 | Forsell | |
| 2011/0196293 A1 | 8/2011 | Forsell | |
| 2011/0196294 A1 | 8/2011 | Forsell | |
| 2011/0196301 A1 | 8/2011 | Forsell | |
| 2011/0201879 A1 | 8/2011 | Forsell | |
| 2011/0257595 A1 | 10/2011 | Forsell | |
| 2011/0270185 A1 | 11/2011 | Forsell | |
| 2011/0270189 A1 | 11/2011 | Forsell | |
| 2011/0270190 A1 | 11/2011 | Forsell | |
| 2011/0270232 A1 | 11/2011 | Forsell | |
| 2011/0276037 A1 | 11/2011 | Forsell | |
| 2011/0288499 A1 | 11/2011 | Forsell | |
| 2012/0059218 A1 | 3/2012 | Forsell | |
| 2012/0245566 A1 * | 9/2012 | Steinbach | 604/891.1 |

FOREIGN PATENT DOCUMENTS

| | | |
|---|---|---|
| WO | WO 02/40083 | 5/2002 |
| WO | WO 2007/051563 | 5/2007 |

OTHER PUBLICATIONS

U.S. Appl. No. 11/591,292 (Forsell) filed Nov. 1, 2006.
U.S. Appl. No. 13/122,917 (Forsell) filed Apr. 6, 2011.
U.S. Appl. No. 13/123,045 (Forsell) filed Apr. 7, 2011.
U.S. Appl. No. 13/123,059 (Forsell) filed Apr. 7, 2011.
U.S. Appl. No. 13/123,069 (Forsell) filed Apr. 7, 2011.
U.S. Appl. No. 13/123,132 (Forsell) filed Apr. 7, 2011.
U.S. Appl. No. 13/123,346 (Forsell) filed Apr. 8, 2011.
U.S. Appl. No. 13/123,573 (Forsell) filed Apr. 11, 2011.
U.S. Appl. No. 13/123,578 (Forsell) filed Apr. 11, 2011.
U.S. Appl. No. 13/123,608 (Forsell) filed Apr. 11, 2011.
U.S. Appl. No. 13/123,619 (Forsell) filed Apr. 11, 2011.
U.S. Appl. No. 13/123,622 (Forsell) filed Apr. 11, 2011.
U.S. Appl. No. 13/123,630 (Forsell) filed Apr. 11, 2011.
U.S. Appl. No. 13/123,654 (Forsell) filed Apr. 11, 2011.

\* cited by examiner

FIG 6
FIG 7
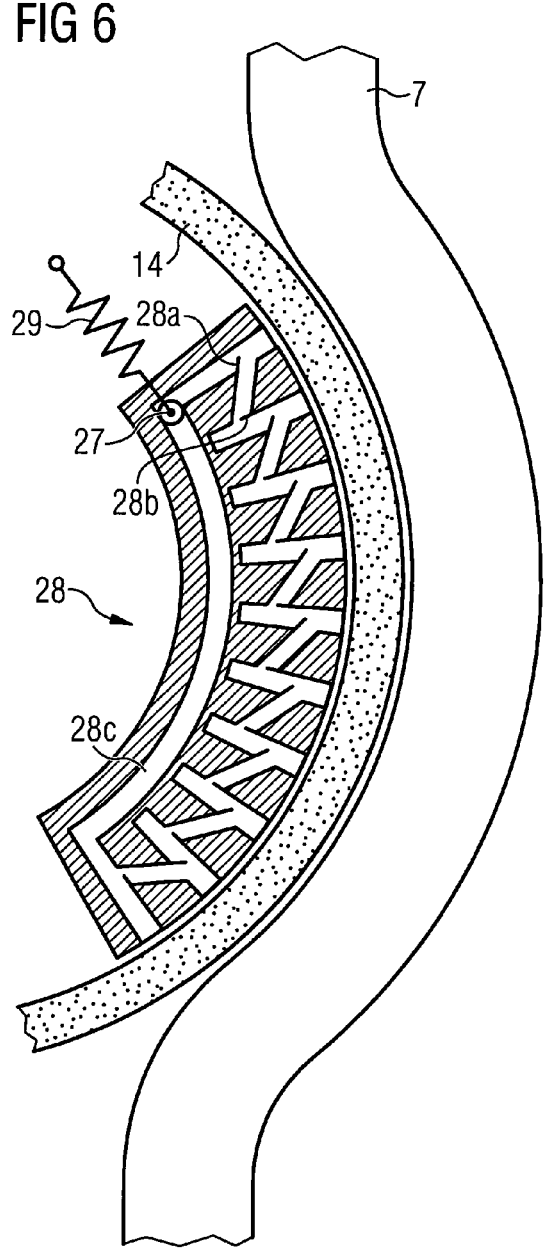
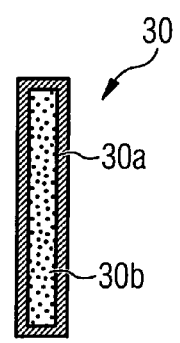

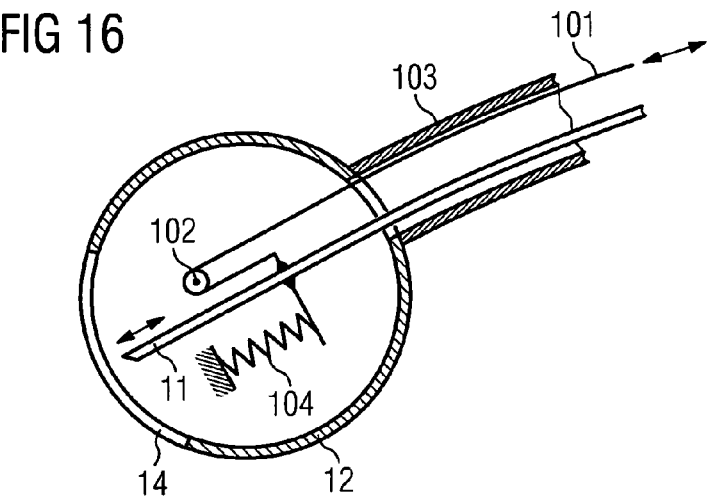
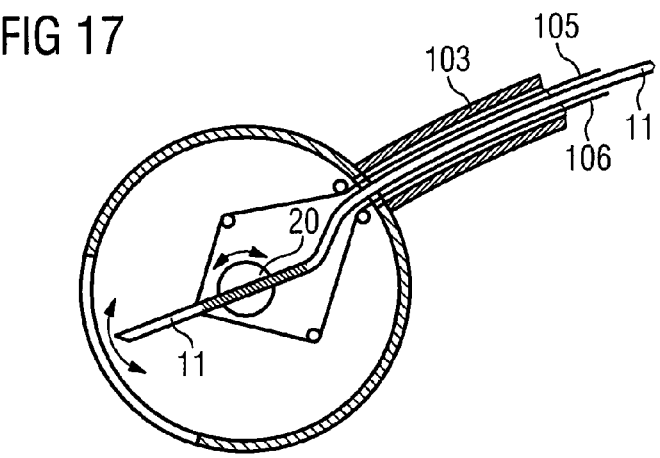
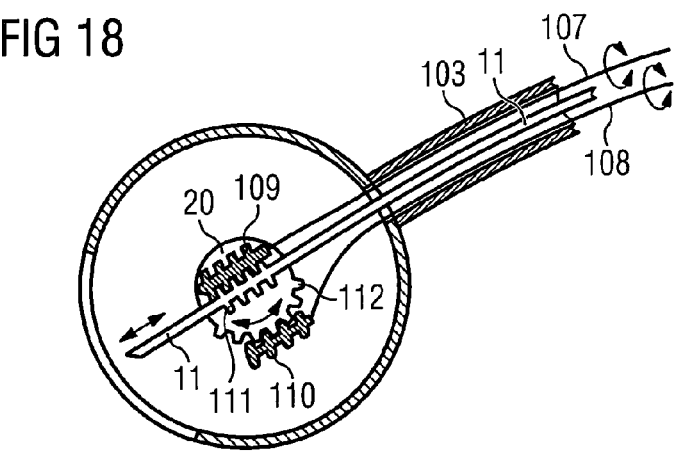

INFUSION OF DRUGS

This application is the U.S. national phase of International Application No. PCT/EP2009/007285, filed 9 Oct. 2009, which designated the U.S. and claims the benefit of U.S. Provisional No. 61/136,876, filed 10 Oct. 2008, the entire contents of each of which are hereby incorporated by reference.

BACKGROUND OF THE INVENTION

The present invention relates to the infusion of a drug into a patient's body in order to stimulate penis erection.

When a male is stimulated erotically, connections between arteries and veins are closed (arteriovenous anastomoses) so that blood which is normally able to bypass the empty spaces or sinuses of the corpora cavernosa is retained in the penis.

The main vessels supplying the blood to the cavernous spaces in the erectile tissue of the corpora cavernosa are the deep arteries of the penis. They are therefore heavily involved in the erection of the penis. They give off numerous branches—the helicine arteries—that open directly into the cavernous spaces. When the penis is flaccid, these arteries are coiled, restricting blood flow. However, the smooth muscle in the coiled helicine arteries relaxes as a result of parasympathetic stimulation. In their relaxed state, the helicine arteries straighten, enlarging their lumina and allowing blood to flow into and dilate the cavernous spaces in the corpora of the penis at arterial pressure. In combination with the bulbospongiosus and ischiocavernosus muscles compressing the veins egressing from the corpora cavernosa, the erectile bodies of the penis become enlarged and rigid, and an erection occurs.

Patients suffering from erectile dysfunction can cause the penis to become turgid by injecting into the corpora cavernosa a medicament, such as papaverine or prostaglandin E1, causing the smooth muscles to relax. The patients have to learn a certain technique under doctor's supervision in order to be able to properly inject the medicament in each of the corpora cavernosa. Only after about 15 minutes after administration of the medicament will the medicament become effective. The entire procedure is inconvenient, the more so as the medicament must usually first be mixed together from a dry substance and a saline solution. Only as a dry substance (and typically cooled) are the available medicaments stable.

Furthermore, proper administration and dosing is critical since the medicament may be transported with the blood into other regions of the patient's body if the injection is not done properly.

Recently, a different method has become known under the brand Muse®. In this method, a plastic rod comprising the medicament alprostadil is inserted into the urethra. Upon pressing a button, the alprostadil is released from the rod into the urethra. After removal of the plastic rod, the penis is rolled between the palms of the hands so that the medicament dissolves, distributes and is absorbed through the urethra wall.

It is the object of the present invention to improve the stimulation of an erection so that the entire process is more convenient for the patient.

SUMMARY OF THE INVENTION

The essence of the invention lies in injecting a substance into the patient's body so as to stimulate penis erection. More specifically, the substance may be injected into both the right and left corpus cavernosum and/or into the two deep arteries thereof and/or possibly into muscle tissue regulating blood flow through the right and left corpus cavernosum and/or into tissue in close proximity to the left and right corpus cavernosum, by means of at least one infusion needle permanently implanted at an appropriate location inside the patient's body. This will greatly improve the patient's comfort as he no longer needs to pierce himself with the infusion needle, which for many people is not an easy task. Furthermore, due to the permanent implantation of the infusion needle, the injection will always occur at the proper location, said location being selected such that the drug is most effective. While there are many conceivable technical variations for injecting the drug through the infusion needle into the patient's body, such injections are definitely more convenient for the patient once the infusion needle has been implanted as compared to the alternative of injecting the drug into the corpora cavernosa manually from outside the penis.

Therefore, according to the invention, a system for stimulating penis erection comprises one or more long, flexibly bendable infusion needles of which the respective tip end or ends are disposed within (at least one) first housing so as to penetrate the first housing's outer wall or walls in at least one penetration area, preferably in two or more different penetration areas. Arranging the infusion needle's tip end in said first housing prevents any fibrosis from growing into the infusion needle. The housing or housings are adapted for implantation inside the patient's body adjacent the two corpora cavernosa and/or the two deep arteries thereof and/or adjacent muscle tissue regulating blood flow through the patient's left and right corpus cavernosum and/or adjacent tissue in close proximity to the two corpora cavernosa. Where the at least one infusion needle is arranged for penetrating the at least one housing in two or more different penetration areas, the distance between the different penetration areas to be penetrated by the at least one infusion needle is selected such that the respective parts of the patient's body are pierced whenever the drug is to be injected. As will be described below, two or more infusion needles may be provided in order to inject the drug in the two or more different penetration areas, or a single infusion needle may be provided along with an appropriate drive unit for displacing the tip end of the infusion needle so as to penetrate the first housing's outer wall in the respective different penetration areas.

The use of long, flexibly bendable infusion needles is chosen for reasons of space constraints in the area where the injection of drugs has to occur. The at least one first housing accommodating the tip end of such long infusion needle or needles can be arranged in close proximity to the injection area so that the tip end can penetrate the outer wall thereof upon advancement of the long infusion needle. The respective other end of the infusion needle or needles, i.e. the infusion needle's rear end, is arranged in a second housing which can be implanted inside the patient's body remote from the first housing in an area with fewer space constraints. The injection needle would be sufficiently long to bridge the distance from the second housing for remote implantation to the first housing and further through the first housing up to the outer wall of the first housing to be penetrated by the needle. Thus, since the respective other end of the infusion needle or needles is remotely implanted within the patient's body, other components of the system cooperating with said other end of the infusion needle may also be implanted remote from the injection area, such as a reservoir for storing the substance to be injected, a pump for advancing the substance from the reservoir to the infusion needle and further through the needle into the patient's body, a motor for actuating the system's active parts, at least one drive unit for—at least—advancing and retracting the infusion needle or needles in such a way that it penetrates the penetration area or areas, so as to allow for stimulation of penis erection by injecting the substance through said penetration area or areas via the at least one infusion needle, and so forth. In a particularly preferred embodiment, the tip end of the infusion needle is advanced by advancing the entire needle from the infusion needle's rear end. It is particularly advantageous to arrange at least a part of the drive unit, preferably the entire drive unit, for advancing the infusion needle within the second housing. More preferably, the reservoir and/or most or all of the active parts, such as the motor, the pump and the like, may also be implanted remotely within the patient's body and, more preferably, may be accommodated in the remotely implanted second housing, whereas the first housing only includes passive elements, possibly including passive elements of the drive unit. In this context it is to be understood that a drive unit according to the present invention includes not only the drive itself, such as an electric motor, but also those components which are involved in transforming the driving energy provided by the drive into movement of the at least one needle, such as transmission gears and the like.

As mentioned above, it is preferred when the at least one drive unit is coupled to the at least one infusion needle so as to—at least—advance and retract the tip end of the at least one infusion needle in such a way that it penetrates at least two different penetration areas within the first housing's outer wall so as to allow for stimulation of penis erection by injecting the substance through said at least two different penetration areas via the at least one infusion needle. For instance, the at least one needle may be arranged for penetrating the at least two different penetration areas either simultaneously (e.g. where a plurality of needles, i.e. at least two needles, are provided) or in immediate time succession (e.g. where a single needle is provided). Preferably, a single command or single action from the patient is sufficient for injecting the substance through the at least two penetration areas, either due to a corresponding mechanical structure of the drive unit or due to a suitably configured control unit controlling the drive unit. This will make the handling of the system easy for the patient.

Where two different penetration areas are pierced in immediate time succession, the time delay between the penetration of the first and the second of the penetration areas is preferably as short as possible, more preferably less than 120 seconds, and most preferably less than 60 seconds. This can be achieved by means of a properly controlled drive unit. A longer time delay would be inconvenient for the patient. Therefore, it is preferred that, once the infusion needle has been retracted from a first of the two penetration areas, it is immediately advanced to the second of the penetration areas.

While it is possible according to one aspect of the invention to actively open the outer wall or walls of the at least one first housing for allowing the infusion needle to penetrate the outer wall, it is preferred according to another aspect of the invention to arrange the needle so as to penetrate the outer wall by piercing through the outer wall. For that purpose, the outer wall may either comprise flaps to be pushed aside by the infusion needle as the infusion needle is advanced, or the outer wall may be made at least in the penetration areas from a material which is self-sealing in respect of penetrations resulting from the at least one infusion needle. While the entire housing may be made from the self-sealing material, it is advantageous for stability reasons if the self-sealing material forms at least one window area in the outer wall, the window area being positioned for penetration by the tip end of the at least one infusion needle. The window area may be formed by a self-sealing penetration membrane which is preferably integrated in the outer wall by press fitting it into the outer wall.

Typically, the self-sealing material would be made from a polymer material which preferably comprises silicone. Other biocompatible polymer materials, such as polyurethane and the like, may be employed as well.

The self-sealing material may also be a composite material. A particularly preferred embodiment of such composite material comprises at least one outer shape-giving layer and a self-sealing soft material contained within the outer layer. Thus, the outer layer forms a shell for the soft material. The outer layer may be made from a biocompatible polymer, such as one of those polymers mentioned above, and preferably the self-sealing soft material may be a gel.

Instead of a self-sealing material, the part of the outer wall to be penetrated by the infusion needle may comprise one or more flaps in the penetration areas through which the infusion needle or needles can pass. This can reduce the force needed for the infusion needle to penetrate the outer wall, as compared to the penetration of a self-sealing membrane. The flap is preferably arranged to be pushed aside by the infusion needle upon advancement of the infusion needle.

Alternatively, the outer wall may comprise at least one door in the penetration areas. A drive is connected to the door for actively opening the door so as to allow for the infusion needle to be advanced through the opened door. Again, the door may comprise a flap, such as a resilient, normally closed flap. It is particularly preferred if the drive connected to the door forms part of the drive unit coupled to the infusion needle. More specifically, the arrangement may be such that advancement of the infusion needle by means of the drive unit simultaneously causes the drive to open the door.

Where a single first housing is provided for the tip end of the at least one infusion needle or where two or more penetration areas are arranged in a single first housing, the penetration areas may be arranged in the housing so that they can be placed either adjacent to both the right and left corpus cavernosum of the patient's penis and/or the two deep arteries of the right and left corpus cavernosum and/or adjacent to muscle tissue regulating blood flow through the right and left corpus cavernosum and/or in sufficiently close proximity to another type of tissue allowing both the first and second corpus cavernosum to become turgid when the particular drug is injected thereinto.

The at least one infusion needle preferably has a tube-like body closed at the tip end and provided with a laterally arranged delivery exit port for delivery of the drug into the particular body part. Therefore, the needle will not cut out any material but will simply divide it during penetration. Thus, when the needle penetrates any material, such as fibrosis and/or the self-sealing penetration membrane, there will be no material entering and blocking the drug delivery passageway.

As mentioned above, a separate infusion needle may be provided for each of the two or more penetration areas. Thus, where injection is desired to occur in only two different areas to provoke penis erection, two separate infusion needles may be advanced through the corresponding penetration area of the respective first housing or housings—preferably simultaneously—and retracted again after injection.

According to a preferred embodiment of the invention, a plurality of two or more infusion needles are provided for each of the different penetration areas and arranged for penetrating different penetration sites within each of said different penetration areas. This allows for penetrating different sites within each penetration area at different times, thereby giving the human tissue time to recover from the piercing by the infusion needle. This can be achieved with a drive unit suitably configured to advance and retract one infusion needle in each of said different penetration areas at one time, and to advance and retract a different infusion needle in each of said different penetration areas at a different time.

The drive unit may be such that the infusion needle is advanced and/or retracted by turning the infusion needle or by turning an element cooperating with the infusion needle. More specifically, the drive unit for advancing and retracting the infusion needle may comprise a screw drive connection. For instance, the drive of the drive unit may turn a screw threadingly engaged with a rack coupled to the infusion needle so that rotation of the screw will cause the infusion needle to be advanced or retracted. The screw and rack of the screw drive connection are preferably accommodated in the remotely implanted second housing but may also be arranged in the housing accommodating the tip end of the needle. Instead of the screw, the infusion needle itself may be rotated by means of a suitable drive so that threading on the needle engaging a fixedly mounted rack causes the infusion needle to advance or retract upon rotation of the infusion needle. Between the first and second housings, the infusion needle is preferably guided in a sheath, so as to reduce friction and prevent growth of fibrosis that might hinder movement of the needle.

The tip ends of a plurality of infusion needles may be contained in a common housing in spaced apart relationship, with the drive unit being configured to advance and retract the tip ends of the infusion needles so as to penetrate the outer wall of the common housing in said at least two different penetration areas, again preferably simultaneously. Placing the tip ends in a common housing simplifies the procedure for fixing the needles in place close to the injection areas. Furthermore, a single drive unit may be used for advancing and retracting the tip ends of the plurality of infusion needles, this making the entire system less voluminous.

According to a particularly preferred aspect of the invention, the tip ends of the plurality of infusion needles are laterally movable, so as to vary the penetration sites within a particular penetration area of the first housing's outer wall, thereby varying the injection site within the particular injection area in the patient's body. As set out above, frequent piercing of the same body part may cause irritation, eventually making further piercing difficult or even impossible. Variation of the injection site by laterally displacing the needle upon each injection cycle may overcome such problems. Accordingly, the at least one drive unit is preferably configured to laterally displace the tip ends of the infusion needles to different penetration sites within each penetration area. More specifically, the drive unit is preferably configured to laterally displace the tip ends of the infusion needles simultaneously. This can be achieved e.g. by jointly mounting the tip ends of the infusion needles on a movable carriage of the drive unit, such as a turntable and/or a shuttle, possibly in the form of a slide. Thus, the drive unit for advancing and retracting the tip ends of the infusion needles is preferably configured so as to also laterally displace the tip ends of the infusion needles each time the tip ends are advanced or retracted.

Thus, the lateral displacement and the advancement/retraction of the tip ends of the infusion needles are coordinated. The lateral displacement of the tip ends of the infusion needles may take place before and/or after an injection. The mechanism may be such that after a certain number of lateral displacements or after lateral displacement over a predefined distance, the tip end of the infusion needle is laterally returned to its initial position so that the next number of infusions will take place again at locations that have previously been penetrated by the needle. It is even preferred to configure the drive unit such that the tip ends of the infusion needles are displaced in at least two different lateral directions. For instance, when the infusion needle has laterally returned to its initial position, the next number of infusions may take place somewhat laterally offset above or below the first number of penetration sites. Thereby, a two-dimensional array of penetration sites can be obtained.

The tip ends of the plurality of infusion needles may be arranged one above the other within a common first housing. Generally speaking, it is preferable in such a situation that the direction of lateral displacement of the tip ends of the infusion needles within different penetration areas is different from, in particular perpendicular to, the direction of distance between the different penetration areas. Alternatively, where the infusion needles are arranged with great lateral distance between each other, the direction of lateral displacement of the tip ends of the infusion needles within each of the different penetration areas may generally be the same as the direction of distance between the different penetration areas.

It is likewise possible to provide the tip end of a single infusion needle within the first housing and to implant the first housing within the patient's body adjacent the two or more injection areas. In this case, the drive unit may be configured so as to laterally displace the tip end of the one infusion needle between various lateral positions such that the infusion needle can penetrate the first housing's outer wall in different penetration areas. The distance of lateral displacement of the single infusion needle between the different penetration areas would amount to 3 mm, 4 mm, 5 mm or even more upon each successive injection. Such successive injections are preferably in immediate time succession, preferably not exceeding 120 seconds between two injections, more preferably not exceeding 60 seconds. Most preferably, the drive unit will be adapted to initiate advancement of the one infusion needle to a second one of the plurality of penetration areas once it has been retracted from a first one of the penetration areas.

An implantable infusion device comprising a single, laterally displaceable infusion needle contained within a housing so as to penetrate the housing's outer wall at different penetration sites is generally known from WO 2007/051563. However, this prior art device is neither intended nor configured for injecting drugs simultaneously or quasi-simultaneously in immediate time succession in two or more different injection areas. The drive unit of the prior art device is instead configured to administer the drug at a different penetration site of a single injection area at each time of operation. For instance, the prior art device may be placed along a blood vessel so as to inject drugs at different injection sites within a single injection area of the blood vessel. Thus, the distance of lateral displacement of the tip end of the infusion needle between one injection and a next following injection is not configured in the prior art device such that different injection areas within the patient's body could be reached. Also, the prior art infusion device is not aimed at being used for the stimulation of penis erection. In addition, in the prior art infusion device the entire infusion needle is accommodated in the housing which is to be implanted next to the constrained injection area, thereby requiring that the drive unit for advancing and retracting the tip end of the infusion needle is also implanted in the same constrained area.

Turning back to the present invention, it is again preferable, when the patient desires to achieve another penis erection at a later point of time, that the single infusion needle does not penetrate the same penetration site within the particular penetration area of the housing's outer wall, but that the drive unit is configured to laterally displace the tip end of the one infusion needle to different penetration sites within each of the different penetration areas. Again, the direction of lateral displacement of the tip end of the one infusion needle within each of the different penetration areas may either be the same as the direction of lateral displacement of the tip end of the infusion needle between the different penetration areas, or may be different from, in particular perpendicular to, the direction of lateral displacement of the tip end of the infusion needle between the different penetration areas. Depending upon the particular configuration of the system, this may be achieved with a single, multifunctional drive unit or with a plurality of different drive units suitably arranged to work in coordinated fashion. Even a combination of these alternatives is possible. For instance, when after a number of infusion cycles the single infusion needle has laterally returned to its initial position, the next number of infusions within the same penetration area may take place somewhat laterally offset above or below the first number of penetration sites. Thus, a two-dimensional array of penetration sites can be obtained in each penetration area, thereby keeping the maximum dimensions of the penetration areas at a minimum. Where the first housing or at least the window area thereof is formed spherically, even a three-dimensional array of penetration sites through the first housing's outer wall can be obtained by means of a suitably adapted drive unit for the needle displacement. This greatly increases the system's flexibility of use.

Regardless of the number of needles involved and regardless of the particular penetration site array to be achieved, it is preferable to configure the drive unit such that the lateral displacement of the tip end of the infusion needle or needles is achieved automatically during advancement and/or retraction of the tip end of the needle or needles. For instance, where the infusion needle is mounted on a movable carriage for the lateral displacement of the tip end of the needle, such as on a turntable or a shuttle, e.g. in the form of a slide, the drive unit may comprise a stepper which is adapted to automatically advance the movable carriage a predefined distance upon each advancement and/or retraction of the infusion needle.

Now, turning to the reservoir, it should be considered that long term storage is not possible with many currently available drugs, this being particularly true of drugs stimulating penis erection. Where long term storage is desired, the drug to be injected would typically be provided as a first substance and mixed with a second substance for injection shortly before the injection is performed. Therefore, according to a preferred embodiment of the present invention, the reservoir of the system comprises at least one first compartment, e.g. for accommodating an infusion liquid such as a saline solution, and at least one second compartment, e.g. containing a drug, in particular a drug in dry form, for mixing with the infusion liquid of the first compartment. The drug may be in powder form and, more specifically, may be a freeze-dried drug. In particular, the drug contained in the second compartment would be a drug for stimulating penis erection. A mixing chamber may be provided for mixing the substance from the first compartment with the substance from one or more of the at least one second compartment.

The number of the second compartments may be huge, such as 50 or more, in particular 100 or more. This would not constitute a particular problem in terms of space constraints since the amount of drugs required for each stimulation of penis erection is extremely little and would amount to a few micrograms. Furthermore, the reservoir may be adapted for implantation within the patient's body remote from the housing containing the needle, such as close to the symphyseal bone. There is a lot of space available above the patient's symphyseal bone, and the drugs could be delivered to the tip end of the needle through an appropriate conduit. If desired, one can inject pure saline solution after the drug injection has been completed so as to clean the conduit and needle from any drug residue. Such cleaning injection could be done through a different penetration area of the housing's outer wall into tissue of the patient which would not affect penis stimulation.

Preferably, the second compartments containing the drug are liquid-tightly sealed against the first compartment, with a mechanism being provided for individually opening a connection between the second compartments and the first compartment.

According to a preferred embodiment, the second compartments are mounted in a plate so as to open towards a first side of the plate and the opening mechanism is adapted to act on the second compartments from a second side of the plate opposite the first side of the plate so that the compartments open to the first side of the plate. Thus, the second compartments may be pushed from their rear side (second side of the plate) so as to open frontward into e.g. a mixing chamber in which the content of the opened second compartments mixes with the content of the first compartment of the reservoir, such as with saline solution. More specifically, the second compartments may be mounted in the plate as displaceable drug containers and the opening mechanism may be adapted to displace the drug containers such that they deliver their drug contents in the manner described.

Alternatively, the plate may be rotatable so as to allow the drug containers to be brought into alignment with a conduit upon rotation of the plate. Thus, when the drug is brought into alignment with such conduit, it may be mixed with e.g. saline solution pumped through the conduit towards the infusion needle.

According to another preferred embodiment, the second compartments are mounted on a tape wound up on a reel. A plurality of rows of the second compartments may be arranged on the tape in side-by-side relationship in a direction different to the winding direction of the tape. This way, the length of the tape can be reduced. It is particularly preferable if the tape is contained in a replaceable cassette. Thus, when all of the second compartments of the tape are emptied, the tape can be easily replaced by replacing the cassette.

As mentioned above, while the reservoir may generally be part of the housing accommodating the at least one infusion needle, it is preferred to arrange the reservoir separate from the housing for remote implantation within the patient's body.

At least a section of a periphery of the first compartment of the reservoir may be made from a flexible material permitting volume changes of the first compartment by deformation of the flexible material as infusion liquid is filled into or drawn out of the reservoir. Thus, the reservoir may be of balloon type. The flexible material may comprise a polymer membrane. A bellows construction is preferable having prebent creases to reduce long term degradation.

According to a particular embodiment, drawing liquid from the reservoir may cause a pressure decrease in at least part of the reservoir so that a negative pressure is attained as compared to the pressure in front of the infusion needle. For instance, the first compartment of the reservoir may comprise a gas chamber and a liquid chamber, said chambers being separated by a membrane, e.g. the polymer membrane. When liquid is drawn from the liquid chamber, the pressure in the gas chamber will decrease accordingly.

The reservoir may have an injection port for injecting liquid from outside the human body into the implanted reservoir. That way, the reservoir implanted in the patient's body along with the infusion device may be kept relatively small since the reservoir can be refilled easily at appropriate time intervals, possibly with a doctor's aid.

Preferably, the injection port comprises a self-sealing material in respect of penetrations caused by a replenishing syringe that would be typically used to refill the reservoir through the patient's skin. It is preferable to implant the self-sealing injection port of the reservoir subcutaneously in the patient's body so that it is easily accessible for refill by means of the syringe.

While it has already been pointed out that drugs, in particular the drugs for stimulating penis erection, may degrade upon long term storage, another important influence on drug degradation is the storage temperature. Some drugs have to be stored in a refrigerator at low or at least moderate temperature. A preferred embodiment of the invention therefore provides for a cooling device for keeping the content within at least one compartment of the reservoir at a temperature below 37° C. This can be achieved with relatively little energy supply if the amount of drugs to be cooled is extremely little, as explained above, and if furthermore the drug compartment within the reservoir is thermally insulated. For instance, the reservoir may be comprised in an insulation chamber.

It is preferred to provide the cooling device with a heat exchanger for exchanging with the patient's body heat generated by the cooling device. Such heat exchanger may be implanted within the patient's body remote from the cooling device to safely dissipate the heat energy in an area where it cannot adversely affect the content of the reservoir.

The cooling device can be of a variety of different types. According to a first embodiment, the cooling device may contain at least two different chemicals reacting with each other, thereby consuming thermal energy which energy is drawn from the contents within the reservoir so that a cooling effect on the contents is achieved. The two chemicals may be provided in separate chambers and a flow control device may be provided to bring together certain amounts of the two different chemicals so as to control the amount of thermal energy drawn from the contents within the reservoir.

According to a second embodiment, the cooling device may comprise at least one Peltier element. A Peltier element is an electrothermal converter causing a temperature difference to occur when an electric current is flowing through the element, based on the Peltier effect. While one part of the Peltier element cools down, a different part thereof heats up. Such heat may again be removed by means of a heat exchanger or simply by providing the particular part generating the heat with an enlarged surface so that the heat is directly dissipated into the adjacent body part of the patient.

According to a third embodiment, the cooling device may be of a refrigerator-type construction. That is, heat exchanging pipes within a chamber to be cooled and heat exchanging pipes outside the chamber for dissipating the heat energy absorbed in the cooling chamber are provided along with a compressor for compressing the refrigerant gas when it exits the cooling chamber and an expansion valve for expanding the refrigerant gas before it re-enters the cooling chamber.

Turning now to the pump for advancing the infusion liquid from the reservoir to the infusion needle or needles, such pump may be a manually driven pump or an automatically driven pump. The manually driven pump may be formed from a balloon which may be manually compressed if suitably arranged under the patient's skin. The balloon type pump may at the same time serve as a reservoir for the infusion liquid, in particular for the saline solution. Preferably, however, an automatically driven pump is used. While the type of pump is not critical, one specific type of pump is particularly preferred. More particularly, an implantable pump preferably comprises a valve device having a first and a second valve member, each having a smooth surface facing each other so as to form a sealing contact between the first and second valve members and further having different liquid channels that can be brought into alignment by displacement of the two smooth surfaces relative to one another while maintaining the sealing contact. This type of pump is described in great detail in WO 2004/012806 A1. The first and second valve members are preferably made from a ceramic material for its excellent sealing capabilities over a long period of time and its inertness to many substances.

The pump may be a membrane type pump, as also described in WO 2004/012806 A1, but is not restricted to this type of pump. The membrane type pump may comprise a membrane displaceable by a piston as the piston moves, the piston being coupled to the valve device so as to slidably displace the first and second valve members relative to one another as the piston moves. Preferably, the pump will be implanted separate from the housing accommodating the needle or needles for remote implantation within the patient's body.

Due to the space constraints within the patient's body in the area where injection is to take place, it is advantageous to implant as many components of the system as possible remote from the first housing accommodating the tip end of the infusion needle or needles. In this context, the drive unit may comprise a mechanical drive element for transmitting kinetic energy from a remote location within the patient's body to the at least one infusion needle. The mechanical drive element may comprise a rotating shaft by which a considerable distance can be bridged within the patient's body. The rotating shaft may, upon rotation about its axis of rotation, cause movement of the infusion needle either directly or indirectly. More specifically, the rotating shaft may be in the form of a worm screw which, when turned, causes the infusion needle or needles to advance and retract and/or causes the infusion needle or needles to move laterally upon each advancement/retraction. Individual rotating shafts or worm screws may be provided for each individual infusion needle and/or for advancing and retracting the tip end of the infusion needle or needles on the one hand and laterally displacing the tip end of the infusion needle or needles on the other hand. Most preferably, the rotating shaft or worm screw is flexibly bendable, so that it can be freely arranged within the patient's body.

Alternatively or in addition, the drive unit may comprise at least one wire directly or indirectly cooperating with the infusion needle so as to cause movement of the infusion needle upon actuation of the wire. Thus, the wire may be pulled at one end thereof which is located within the patient's body remote from the injection sites. Preferably, the wire extends through the same conduit which connects the infusion needle or needles with the reservoir. More specifically, pulling the wire may cause the tip end of the infusion needle or needles to displace laterally from a first to a second penetration areas or from a first penetration site to a second penetration site within a single one of the different penetration areas. A single pulling wire may be sufficient to cause movement of the infusion needle in one direction, whereas a spring element or any other pretensioning means may be provided to urge the infusion needle back to the initial starting position or to a different starting position. Alternatively, two pulling wires may be provided to move the infusion needle back and forth in a single dimension.

According to a preferred embodiment, the tip end of the at least one infusion needle is arranged for two-dimensional lateral displacement. This can be achieved by means of two pulling wires, preferably cooperating again with spring elements or other pretensioning means to provide a counterforce to be overcome by pulling the wires. Alternatively, three pulling wires may be provided to laterally displace the tip end of the infusion needle back and forth along at least two directions within a two-dimensional plane.

A pulling wire may also be arranged to advance or retract the infusion needle by pulling the wire. Again, a spring element or other pretensioning means may be provided to urge the infusion needle back to its initial starting position or to a different starting position.

Alternatively, the drive unit may comprise a hydraulic drive for transmitting hydraulic energy to the at least one infusion needle for advancing the tip end thereof and/or for laterally displacing the tip end thereof. The infusion liquid itself may be used as the hydraulic medium providing the hydraulic energy, or a secondary liquid different from the infusion liquid may be used.

Further alternatively, the drive unit may comprise one or more electric motors preferably inside the second housing accommodating the respective other end of the at least one infusion needle. In this case, energy may be transmitted from a remote location within the patient's body to the at least one motor by means of appropriate wiring. Again, as in the two afore-described alternatives, a single motor may be provided for advancing and retracting the tip end of the infusion needle or needles and for laterally displacing the tip end of the infusion needle or needles, or individual motors may be provided for each individual infusion needle and/or for advancing the tip ends of the infusion needle or needles on the one hand and laterally displacing the infusion needle or needles on the other hand.

Even further alternatively, the drive unit may comprise an electromagnetic drive for laterally displacing and/or for advancing and retracting the tip end of the infusion needle or needles. For instance, the electromagnetic drive may comprise a group of electromagnets composed of a plurality of laterally spaced apart electromagnet first parts and at least one electromagnet second part, the electromagnet second part cooperating with an energized one of the electromagnet first parts. The electromagnet second part is fixedly connected to the infusion needle or needles either directly or indirectly so that upon energization of one or more of the electromagnet first parts the electromagnet second part and, thus, the infusion needle or needles will be caused to move. The arrangement of the electromagnet first parts and second part may be such that the electromagnet first parts are arranged in a first plane and the electromagnet second part is movable in front of or behind the first plane. Alternatively, the electromagnet first parts may face each other, thereby defining a first plane between them, and the electromagnet second part may be movable within the first plane. Depending on which one or ones of the electromagnet first parts are energized, the electromagnet second part with the infusion needle or needles fixed thereto will move accordingly. The electromagnet first parts preferably each include a magnetic coil.

In either one of the aforementioned alternatives, it is advantageous to transmit the driving energy through the conduit that connects the first and second housings. That is, in the case of a mechanical drive element in the form of a wire or rotating shaft, the wire/shaft and the infusion liquid may be guided through a common conduit. The common conduit may comprise two separate paths, one for the shaft or wire and one for the at least one infusion needle. Such a common conduit facilitates the handling and arrangement of the system during implantation. Similarly, the wiring for transmitting electric energy to the motor or to the electromagnetic drive may be guided through a conduit connecting the infusion needle or needles with the reservoir.

Where the pump and/or drive unit is not actuated manually, a drive in the form of a motor may be arranged e.g. for electrically, magnetically or electromagnetically actuating the pump and/or drive unit or for hydraulically actuating the pump and/or drive unit. The motor is preferably arranged for actuating either the pump or the drive unit, thereby causing simultaneous actuation of the other, e.g. the drive unit or the pump. A motor may also be provided for actuation of any other energy consuming part of the infusion device. More specifically, a plurality of motors may be provided, e.g. an individual motor for each infusion needle and/or an individual motor for displacing the tip end of the infusion needle in a lateral direction on the one hand and for advancing the tip end of the infusion needle through the housing's outer wall on the other hand.

Again, for reasons of space constraints in the area of implantation of the first housing or housings accommodating the tip end or ends of the at least one infusion needle, it is advantageous to remotely implant the motor within the patient's body separate from the first housing, preferably close to or within the second housing. Again, actuating means may be provided for manual activation of the motor or motors, such actuating means preferably being adapted for subcutaneous implantation.

The term "motor" according to the present invention includes anything that employs energy other than manual power and either automatically transforms such energy into kinetic or hydraulic or another type of energy or directly uses such energy to activate the pump, drive unit and/or other part of the overall system. As such, it is possible that part of the drive unit also forms part of the motor, e.g. in the case of an electromagnetically actuated drive unit.

Coupling elements may be provided either for conductive or for wireless energy transfer from outside the patient's body to the motor. For instance, the motor may be arranged for being wirelessly driven by an external electromagnetic field.

An energy source for providing energy to at least one of the pump, the drive unit and the drive (motor) for driving the drive unit, and any other energy consuming part of the system may be provided. For instance, an external energy source for use outside the patient's body, such as a primary energy source or a battery, in particular a rechargeable battery, that may be mounted on the patient's skin, may be used to provide energy to the pump and/or drive unit and/or any other energy consuming part of the system. The energy source may in particular be connected to the at least one motor for actuating these components. An external energy source for wireless energy transfer may be adapted to create an external field, such as an electromagnetic field, magnetic field or electrical field, or create a wave signal, such as an electromagnetic wave or sound wave signal.

Where the energy is wirelessly transferred to the implanted components, a transforming device for transforming the wirelessly transferred energy into electric energy may be provided. Such transforming device is preferably adapted to be placed directly under the patient's skin so as to minimize the distance and the amount of tissue between the transforming device and the energy supply means outside the patient's body.

Instead of or in addition to an external energy source, the system may comprise an implantable energy source. While such implantable energy source may be part of or may be contained within the housing accommodating the infusion needle or needles, it is preferred to provide the implantable energy source separate from the housing for remote implantation within the patient's body. Such implantable energy source preferably comprises energy storage means, such as a long-life battery or, more preferably, an accumulator. The accumulator has the advantage of being rechargeable. Preferably, the accumulator comprises a rechargeable battery and/or a capacitor.

Again, coupling elements for conductive or wireless energy transfer from a primary energy source outside the patient's body to the accumulator may be provided for charging the accumulator from outside the patient's body when the device is implanted in the patient's body. Similarly, the accumulator may comprise coupling elements for conductive and/or wireless energy supply to the at least one motor of the infusion device.

A feedback subsystem, which may be part of a control unit described below, can advantageously be provided to wirelessly send feedback information relating to the energy to be stored in the energy storage means from inside the human body to the outside thereof. The feedback information is then used for adjusting the amount of wireless energy transmitted by the energy transmitter. Such feedback information may relate to an energy balance which is defined as the balance between an amount of wireless energy received inside the human body and an amount of energy consumed by the at least one energy consuming part. Alternatively, the feedback information may relate to an energy balance which is defined as the balance between a rate of wireless energy received inside the human body and a rate of energy consumed by the at least one energy consuming part.

Preferably, a control unit is provided for controlling an amount of infusion liquid to be administered through the at least one injection needle. A single command from the patient to the control unit, such as a single actuation of a press button or other type of switch, is sufficient for causing the control unit to control the injection of the drugs at two different locations within the patient's body. The control unit may be provided for controlling at least one of the pump, the drive unit and the motor and any other energy consuming part of the system and, where the system includes an internal or external energy source, said energy source. Again, the control unit is preferably separate from the housing accommodating the infusion needle or needles so as to be implantable within the patient's body. The control unit may be adjusted such that the appropriate amount of drugs will be administered at the appropriate time to the particular one of the injection sites. Automatic administration will substantially relieve the patient.

Preferably, the control unit has a data transfer port for data transfer between an external data processing device outside the patient's body and the control unit implanted in the patient's body, regardless of whether the control unit is contained in the housing accommodating the infusion needle or needles or whether it is implanted within the patient's body remote from said housing. The data transfer port allows for monitoring the control unit to adapt the system to changing needs of the patient. Preferably, the data transfer port is a wireless transfer port for the data transfer, so as to provide easy data exchange between the control unit and the external data processing device, e.g. during a visit to the doctor. Most preferably, the control unit is programmable to further increase its adaption flexibility. Instead of or in addition to the external data processing device, the control unit may comprise an external component for manual operation by the patient for setting into operation the control unit.

Apart from or as a part of the control unit, feedback may be provided on parameters relevant for the treatment. Such parameters may be either physical parameters of the patient and/or process parameters of the system. For this purpose, at least one feedback sensor is provided for detecting such parameters. For instance, the feedback sensor may be adapted to detect one or more parameters relating to any of the following: drug level, flow volume in blood vessel, pressure, electrical parameters, distension, distance, etc.

The feedback sensors may be connected to the control unit and the control unit may comprise a control program for controlling drug delivery in response to one or more signals from the feedback sensors. In addition or alternatively, feedback data may be transferred from the control unit to the external data processing device. Such feedback data may be useful for the doctor's diagnosis.

The penetration areas of the wall or walls of the first housing or housings within which the tip end of the infusion needle or needles are disposed may be arranged in the patient's body at various locations. For instance, they may be arranged adjacent the left and right corpora cavernosa and/or the two deep arteries running through the left and right corpora cavernosa and/or muscle tissue regulating blood flow through the patient's left and right corpora cavernosa and/or another kind of tissue in close proximity to the left and right corpora cavernosa.

A holder may be used to secure the corpora cavernosa to the first housing or housings so that the housing rests in place.

Other components of the system are preferably remotely implanted, such as adjacent the patient's symphyseal bone. As discussed above, some components of the system may be implanted subcutaneously. Subcutaneous implantation increases the possibilities of wireless energy and/or data transfer between the implanted and the extracorporal parts of the system. Also, refilling the reservoir through an injection port by means of a replenishing needle penetrating through the patient's skin is substantially facilitated when an injection port of the reservoir is implanted subcutaneously. In particular, the compartment of the reservoir containing the saline solution might need to be refilled frequently, whereas the other compartments comprising individual small doses of the drug would need no refill. It should be understood, however, that depending upon the circumstances any implantable component of the system may be placed in the abdomen or even in the thorax. Activating means for direct manual operation by the patient may also be provided to be implanted subcutaneously, e.g. for setting into operation one or more of the aforementioned motors or for simply setting into operation the control unit of the system. Such activating means may be in the form of a subcutaneously implantable switch manually operable by the patient from outside the patient's body.

The various aforementioned features of the invention may be combined in any way if such combination is not clearly contradictory. The invention will now be described in more detail in respect of preferred embodiments and with reference to the accompanying drawings. Again, individual features of the various embodiments may be combined or exchanged unless such combination or exchange is clearly contradictory to the overall function of the device.

BRIEF DESCRIPTION OF THE DRAWINGS

FIG. 6 shows a plan view of a part of the infusion device of FIGS. 4 and 5, FIG. 7 shows a cross-sectional view through a penetration membrane made from a composite material, FIG. 16 shows a ninth embodiment with a principle of advancing and retracting an infusion needle by means of a pull wire, FIG. 17 shows a tenth embodiment with a principle of laterally displacing an infusion needle by means of pull wires, FIG. 18 shows an eleventh embodiment with a principle of advancing and retracting an infusion needle and laterally displacing an infusion needle by means of rotating shafts.

DETAILED DESCRIPTION OF THE DRAWINGS

Figure 1:
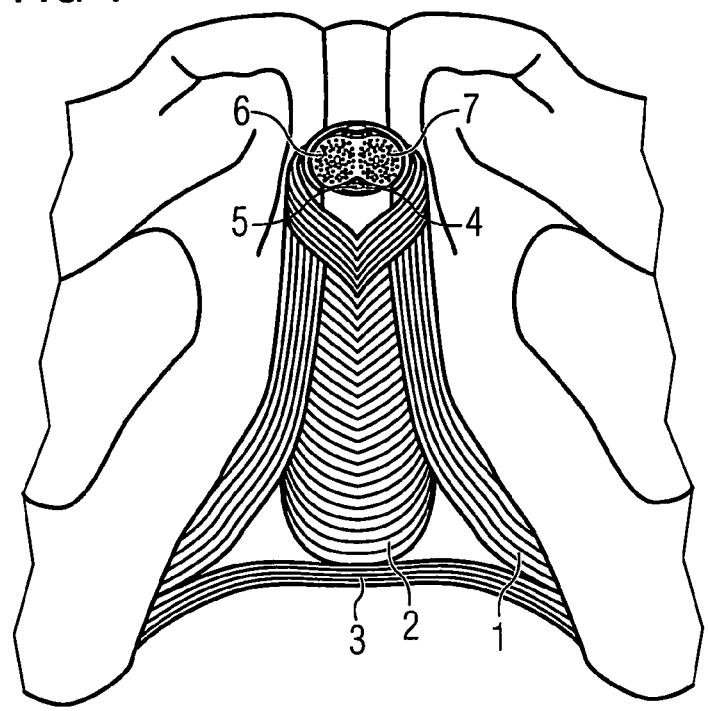
FIG. 1 shows the muscles of the perineum.
Figure 2:
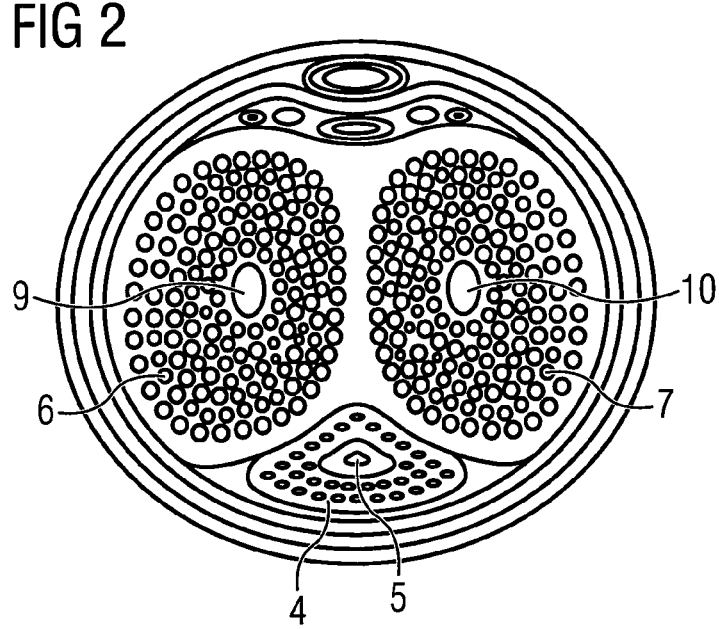
FIG. 2 shows a cross-section through the penis.

FIG. 1 shows the muscles of the perineum of a male. Reference numerals 1, 2 and 3 designate the ischiocavernosus muscles, bulbospongiosus muscles and superficial transverse perineal muscles, respectively. The bulbospongiosus muscle surrounds lateral aspects of the bulb of the penis at the most proximal part of the body of the penis inserting into the perineal membrane, and further surrounds the dorsal aspect of the corpus spongiosum 4 surrounding the urethra 5 and the left and right corpora cavernosa 6, 7. The ischiocavernosus 1 embraces the crus of the penis, inserting onto the inferior and medial aspects of the crus and to the perineal membrane medial to the crus. While the bulbospongiosus muscle assists the erection by compressing outflow via the deep perineal vein and by pushing blood from the bulb into the body of the penis, the ischiocavernosus muscle 1 maintains erection of the penis by compressing outflow veins and pushing blood from the root of the penis into the body of the penis. FIG. 2 is a cross-sectional view through the penis. As can be seen, the penis is composed of three cylindrical bodies of erectile cavernous tissue: the paired corpora cavernosa 6, 7 dorsally and the single corpus spongiosum ventrally. Deep arteries 9, 10 run distally near the center of the corpora cavernosa, supplying the erectile tissue in these structures. The deep arteries of the penis are the main vessels of the cavernous spaces in the erectile tissue of the corpora cavernosa and are therefore involved in the erection of the penis. They give off numerous branches that open directly into the cavernous spaces. When the penis is flaccid, these arteries are coiled, restricting blood flow.

Figure 3:
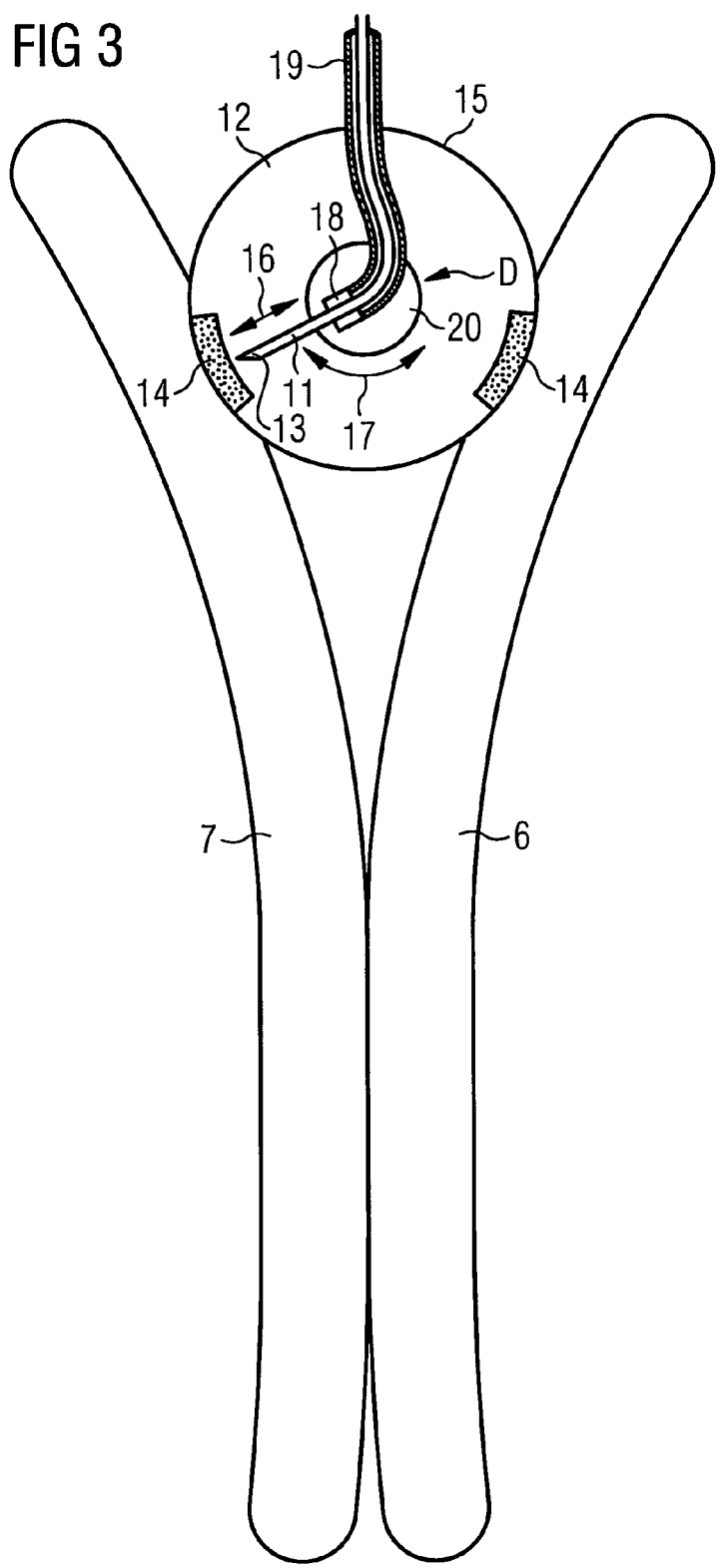
FIG. 3 shows a first embodiment including a single long and flexible infusion needle.

For reasons of simplification, the following figures only display the corpora cavernosa 6, 7. FIG. 3 shows a part of the system according to a first embodiment. More specifically, a single long and flexibly bendable infusion needle 11 is arranged with its tip end 13 in a first housing 12, wherein the tip end 13 of the needle 11 is positioned such that it can be advanced and retracted through a self-sealing window area 14 in the housing's 12 outer wall 15 in a longitudinal direction 16, so as to pierce the corpus cavernosum 6 or 7 located adjacent the window area 14.

Two window areas 14 are provided in the outer wall 15 of the first housing 12, one adjacent each of the two corpora cavernosa 6, 7. The infusion needle is displaceable in a lateral direction 17 between the two window areas 14 by means of a drive unit D. The same drive unit D or a different drive unit may cause the infusion needle 11 to be advanced and retracted. It is preferred that the drive unit for advancing and/or retracting the infusion needle, or at least the drive thereof, is disposed in a second housing which accommodates the respective other end of the infusion needle 11 and which is remotely implanted in the patient's body. For the purpose of enabling the tip end of the infusion needle to be advanced and retracted, the infusion needle 11 is mounted on a slide 18 for longitudinal movement. A conduit 19 is connected to the first housing 12 guiding the infusion needle 11 therein and, thus, protecting the infusion needle 11 against overgrowth with fibrosis. The conduit 19 continues to guide the infusion needle within the first housing up to the slide 18 and is fixed to the slide so as to perform the function of a Bowden cable system, i.e. preventing the front part of the infusion needle 11 from flexing away when the tip end 13 of the needle is advanced through the window area 14.

In operation, the infusion needle 11 will first be advanced with the tip end 13 thereof to penetrate one of the two self-sealing penetration windows 14, injection fluid containing a drug for stimulation of penis erection will be injected into the corpus cavernosum 7 through the infusion needle 11 and, thereafter, the infusion needle 11 will be retracted again. Upon retraction of the infusion needle, the infusion needle will be laterally displaced along the direction 17 so that the tip end 13 thereof comes to lie in front of the other of the two self-sealing window areas 14, the infusion needle 11 will be advanced again so that infusion liquid can be injected through the tip end 13 thereof into the other corpus cavernosum 7 and then the infusion needle 11 will be retracted again. At the end of this procedure, the infusion needle 11 will return to its initial position shown in FIG. 3.

The structure of the system shown in FIG. 3 may be purely mechanical. For instance, as will be described in more detail below, the pressure with which the infusion liquid is advanced through the needle 11 may in cooperation with spring elements cause the needle 11 to be advanced, retracted and laterally displaced to the other window area 14. Thus, after two pulses of injection fluid advanced through the conduit 19 towards the needle 11, the needle 11 will automatically return to its starting position shown in FIG. 3.

Figure 4:
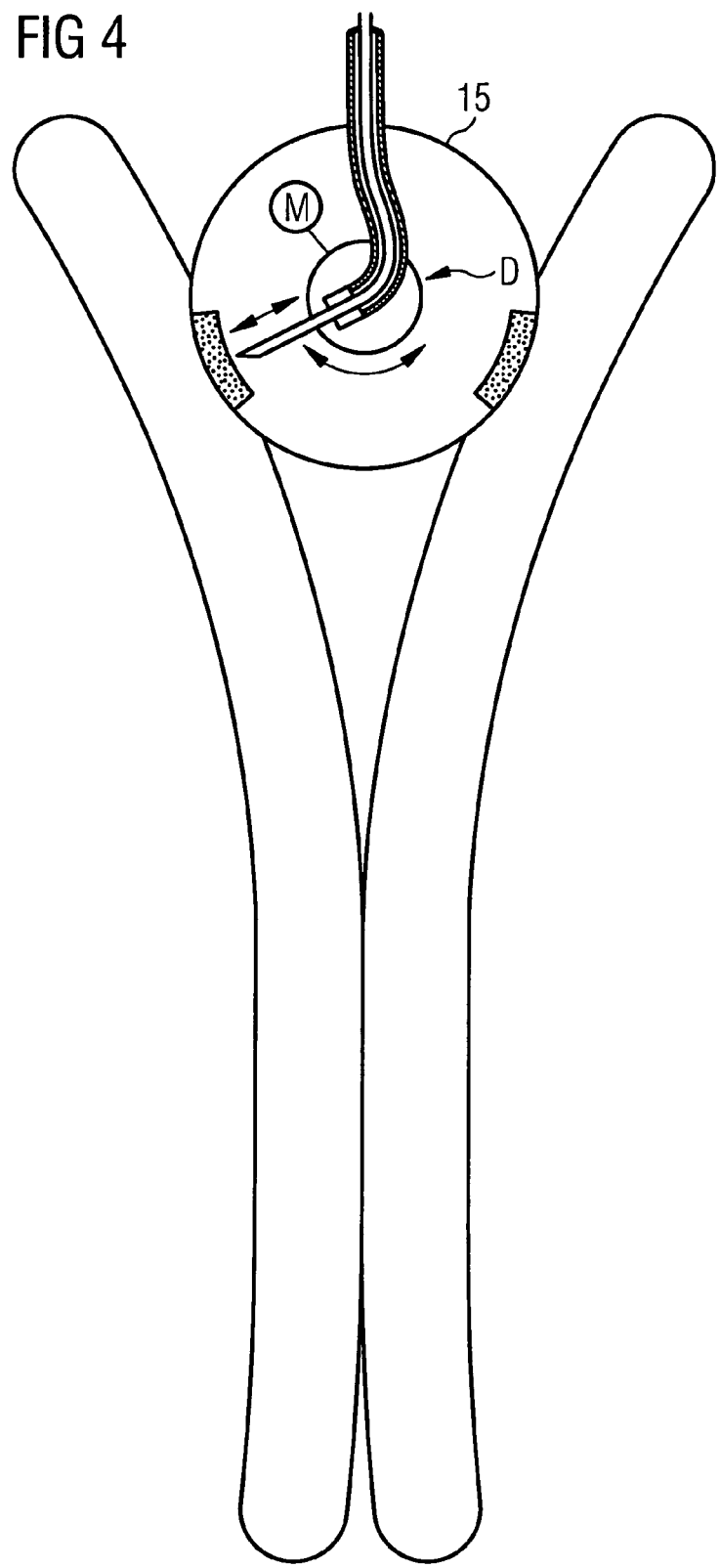
FIG. 4 shows a second embodiment including a single infusion needle and a motor accommodated in a common housing.

However, it is likewise possible to incorporate a motor M or a plurality of motors M within the first housing 12 in order to achieve the desired needle displacement by means of the drive unit D. This is schematically shown in FIG. 4. Of course, the motor M will have to be provided with energy and will need to be controlled in an appropriate manner so as to obtain the desired effect. This is not specifically shown in FIG. 4. The energy is preferably transmitted to the motor M from an energy source either remotely implanted inside the patient's body or provided externally of the patient's body. The number and size of the motors M in the first housing 12 should be kept at a minimum for reason of space constraints. Instead, the motors are preferably arranged remote from the first housing 12 in proximity to or within the afore-mentioned second housing.

The drive D may be configured such that after each penetration cycle (consisting of two injections) the infusion needle 11 stops at a position different from the starting position so that the tip end 13 thereof penetrates the window areas 14 in the next following injection cycle at different sites as compared to the foregoing injection cycle.

Figure 5:
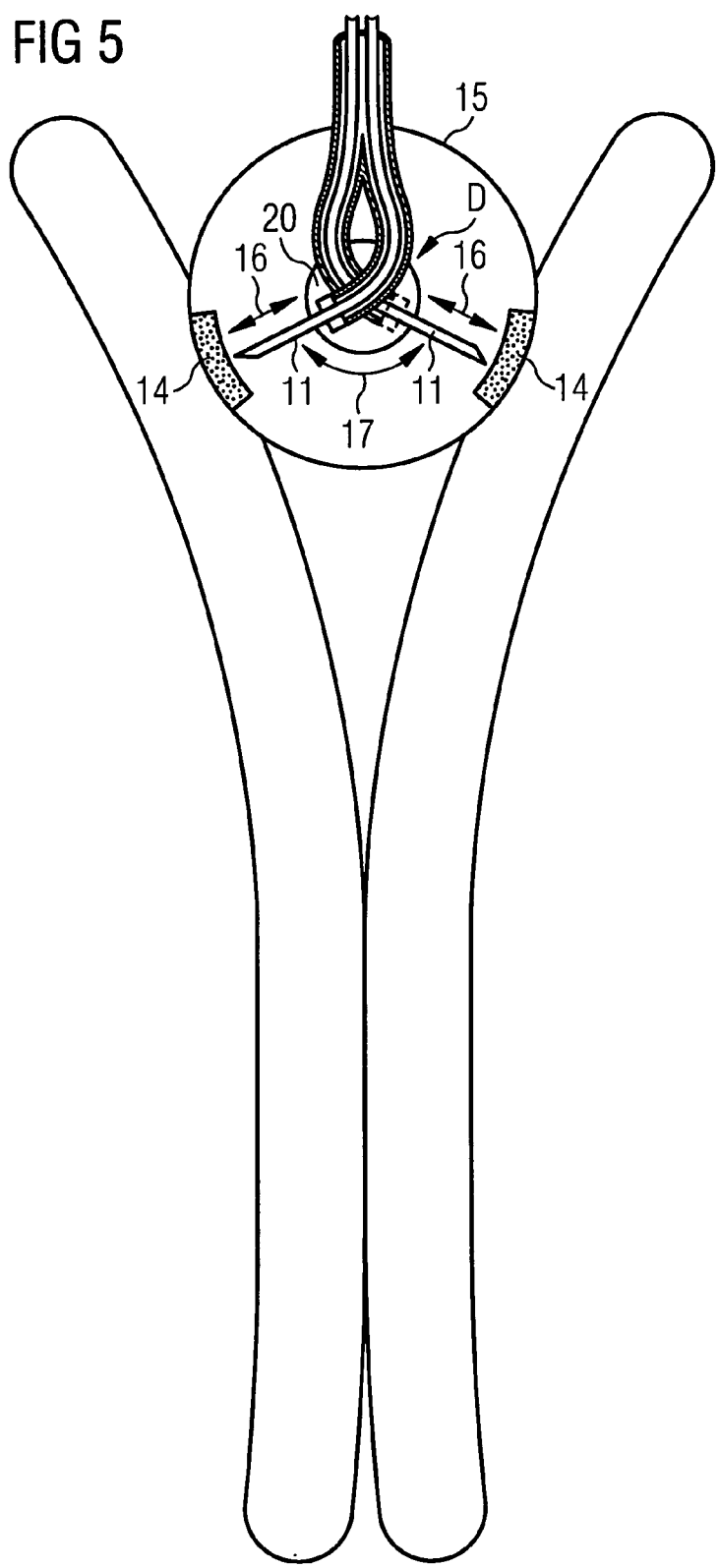
FIG. 5 shows a third embodiment including the tip ends of two long and flexible infusion needles in a common housing.

FIG. 5 shows a third embodiment which differs from the first and second embodiments in that it comprises two infusion needles 11 guided within a common sheath or conduit 19 up to the first housing's outer wall 15 and guided within the first housing in separate sheaths. Thus, when both infusion needles 11 are advanced and retracted simultaneously along the direction 16, injection of infusion liquid occurs at exactly the same time. The drive unit D or a different drive unit may be used to turn the turntable 20 on which the tip ends of the infusion needles 11 are mounted, stepwise in the direction 17 so that the window areas 14 will be penetrated by the tip ends of the infusion needles 11 at different penetration sites during the next following injection cycle. Again, one or more motors M, not shown in FIG. 5, may be used for driving one or more of the components of the drive unit D.

The principle of a guide structure for laterally displacing the tip end of the infusion needle will now be described in context with FIG. 6. Such guide structure may be used e.g. for each of the two infusion needles 11 shown in FIG. 5 or may also be used slightly modified for the lateral displacement of the infusion needle 11 shown in FIGS. 3 and 4.

The guide structure 28 is securely fixed adjacent the self-sealing window area 14 which itself is implanted adjacent the patient's corpus cavernosum 7. The guide structure 28 comprises a guide pin 27 securely connected to the tip end of the infusion needle 11 (not shown) such that the infusion needle 11 cooperates with the guide structure 28. Upon advancement or retraction of the infusion needle 11, the guide pin 27 will be guided in the guide structure 28 and thereby laterally displace the tip end of the infusion needle 11, which lateral displacement causes rotation of the turntable 20 (not shown in FIG. 6). Resilient flaps 28a, 28b within the guide structure 28 serve to guide the guide pin 27 through the entire guide structure 28 upon repeated advancement and retraction of the infusion needle 11. The guide structure 28 is designed to provide different penetration sites through the self-sealing window area 14 into the corpus cavernosum 7. Where it is desired, the trajectory of guide structure 28 may include a return path 28c for the guide pin 27 to return to its starting position shown in FIG. 6. Such return action will be caused by a return spring 29 which is permanently fixed to a rigid part of the first housing.

The same structure can likewise be used in the embodiments shown in FIGS. 3 and 4 to displace the tip end of the single infusion needle 11 laterally between the two window areas 14. Of course, the structure would have to be slightly adapted to accommodate for the larger distance to be overcome between the two window areas 14.

FIG. 7 shows a preferred embodiment of a penetration membrane to be used as the self-sealing window area 14 in the outer wall 15 of the housing 12. The penetration membrane 30 is made from a composite material. The same material can also be used for other flexible wall portions or for an infusion port that will be described below in connection with another embodiment. The composite material of penetration membrane 30 shown in FIG. 7 comprises an outer shape-giving layer 30a defining a volume in which a self-sealing soft material 30b is contained. Self-sealing soft material 30b can be of gel type having a viscosity such that it does not flow through any penetrations caused by the infusion needle 11 during penetration of the outer shape-giving layer 30a. Instead of a single outer shape-giving layer 30a, the shape-giving layer 30a may comprise a plurality of layers. The outer shape-giving layer 30a preferably comprises silicone and/or polyurethane, since such materials can be produced to have self-sealing properties in respect of penetrations resulting from the infusion needle 11.

Figure 8:
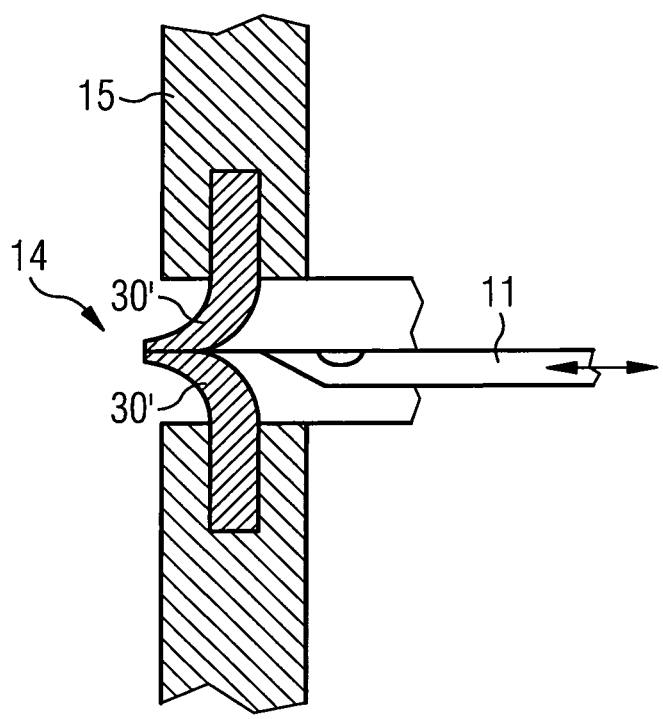
FIG. 8 shows a cross-sectional view through the outer wall with flaps in the penetration area.

Instead of a self-sealing membrane, the window area 14 in the outer wall 15 of the housing 12 may be formed by one or more flaps, as shown in FIG. 8. Two flaps 30' being made from a resilient, biocompatible material are arranged so as to form a slit which is normally closed and through which the infusion needle 11 can pass when it is advanced. Upon advancement of the infusion needle 11, the needle's tip end will push aside the normally closed flaps 30', and when the needle 11 is retracted again, the flaps 30' will return to their normally closed position so as to form a seal against ingression of body liquid.

Figure 9:
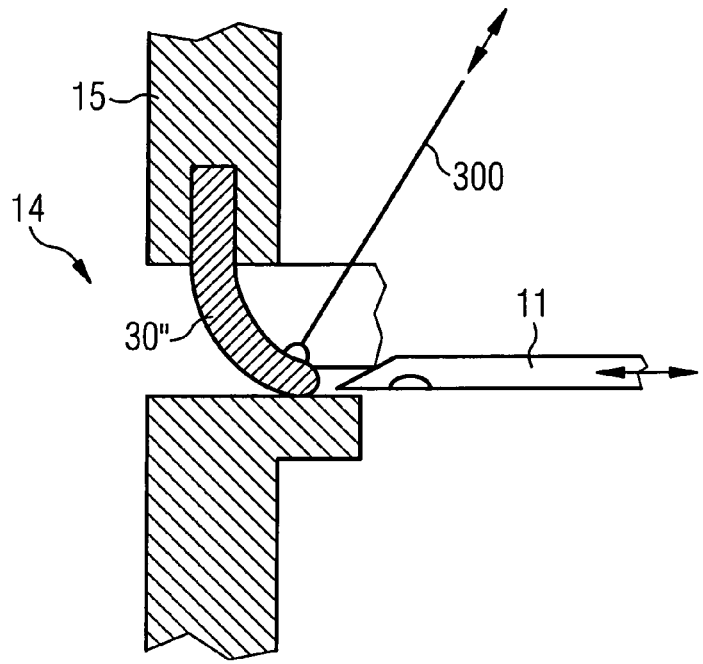
FIG. 9 shows a cross-sectional view through the outer wall with an actively openable door in the penetration area.
Figure 10:
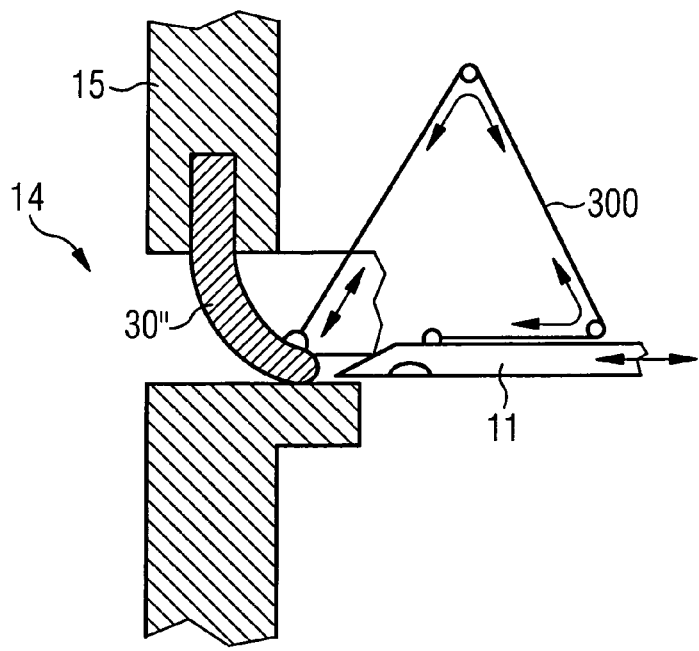
FIG. 10 shows a cross-sectional view through the outer wall with an actively openable door according to another embodiment.

FIG. 9 shows a different embodiment. In this case, the self-sealing window 14 in the outer wall 15 comprises a door 30" which can be opened by mechanical action. In the embodiment shown, the door is formed by a flap made from a resilient, biocompatible material which keeps the window area 14 closed in its normal position. A pull wire 300 is attached to one end of the door 30" in order to allow for opening the door by pulling the pull wire 300. The pull wire 300 or any other drive connected to the door 30" forms part of the drive unit coupled to the front part of the infusion needle 11. For instance, as is shown in FIG. 10, the pull wire 300 may be attached directly to the infusion needle 11 so that advancement of the infusion needle 11 will simultaneously cause the door 30" to be lifted up so that the infusion needle 11 can pass underneath the door 30" and thus penetrate the outer wall 15 easily. Due to the resiliency of the door material, the door 30" will automatically close when the force, such as the pulling force exerted via the pull wire 300, is released. Instead or in addition, the closing action may be supported by at least one spring element urging the door into its closed position.

Figure 11:
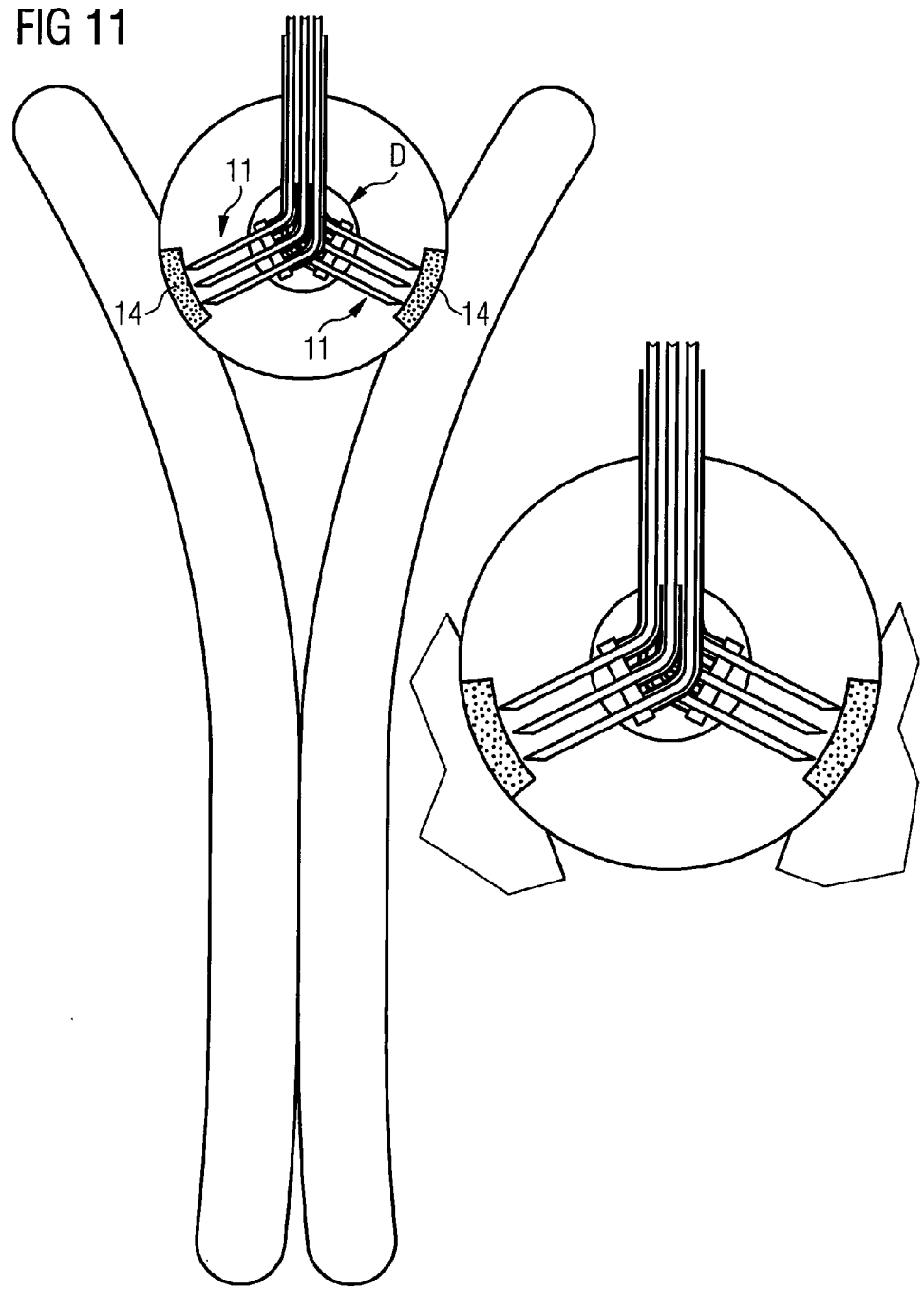
FIG. 11 shows a fourth embodiment including the tip ends of a plurality of infusion needles within a common housing.

FIG. 11 shows a fourth embodiment comprising a plurality of infusion needles for each of the two window areas 14. In this embodiment it is not necessary to provide a turntable by which the needles can be pivoted stepwise in order to laterally displace the needles from one penetration site to a different penetration site within the same window area 14. Instead, upon successive injection cycles a different one of the plurality of injection needles will be advanced and retracted for each of the two window areas 14. Thus, the effect achieved is the same as in the embodiment shown in FIG. 5.

Figure 12:
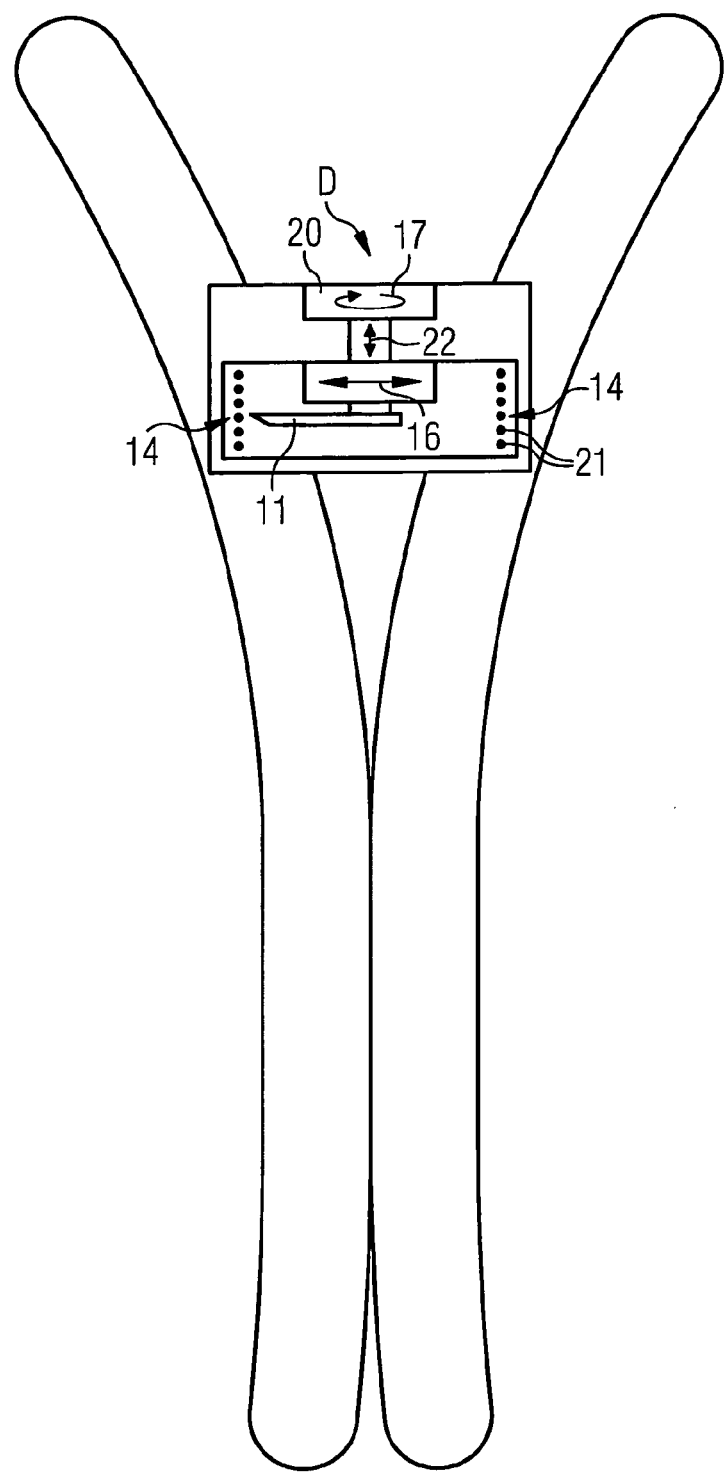
FIG. 12 shows a fifth embodiment comprising a single infusion needle, the tip end of which is laterally and vertically displaceable.

FIG. 12 shows a fifth embodiment which differs from the first and second embodiments shown in FIGS. 3 and 4 in that the tip end of the single infusion needle 11 is not only laterally displaceable in the direction 17 between the two window areas 14 but also laterally displaceable between different penetration sites 21 within the same penetration area 14. More specifically, the direction of lateral displacement of the tip end of the infusion needle 11 within each of said different penetration areas 14 is perpendicular to the direction of lateral displacement between the different penetration areas 14. To achieve this result, the drive unit D is configured to longitudinally advance and retract the infusion needle 11 along a direction 16, to pivot the tip end of the infusion needle 11 by means of a turntable 20 between the two penetration areas 14 along a pivoting direction 17 and to raise or lower the tip end of the infusion needle 11 along a third direction 22 perpendicular to the longitudinal direction 16. A suitable purely mechanical construction may perform this function. However, one or more motors may also be provided to perform one and/or the other of these functions. The motor or motors and, in particular, the drive unit for advancing and retracting the infusion needle are preferably provided remote from the first housing, as already mentioned previously.

Figure 13:
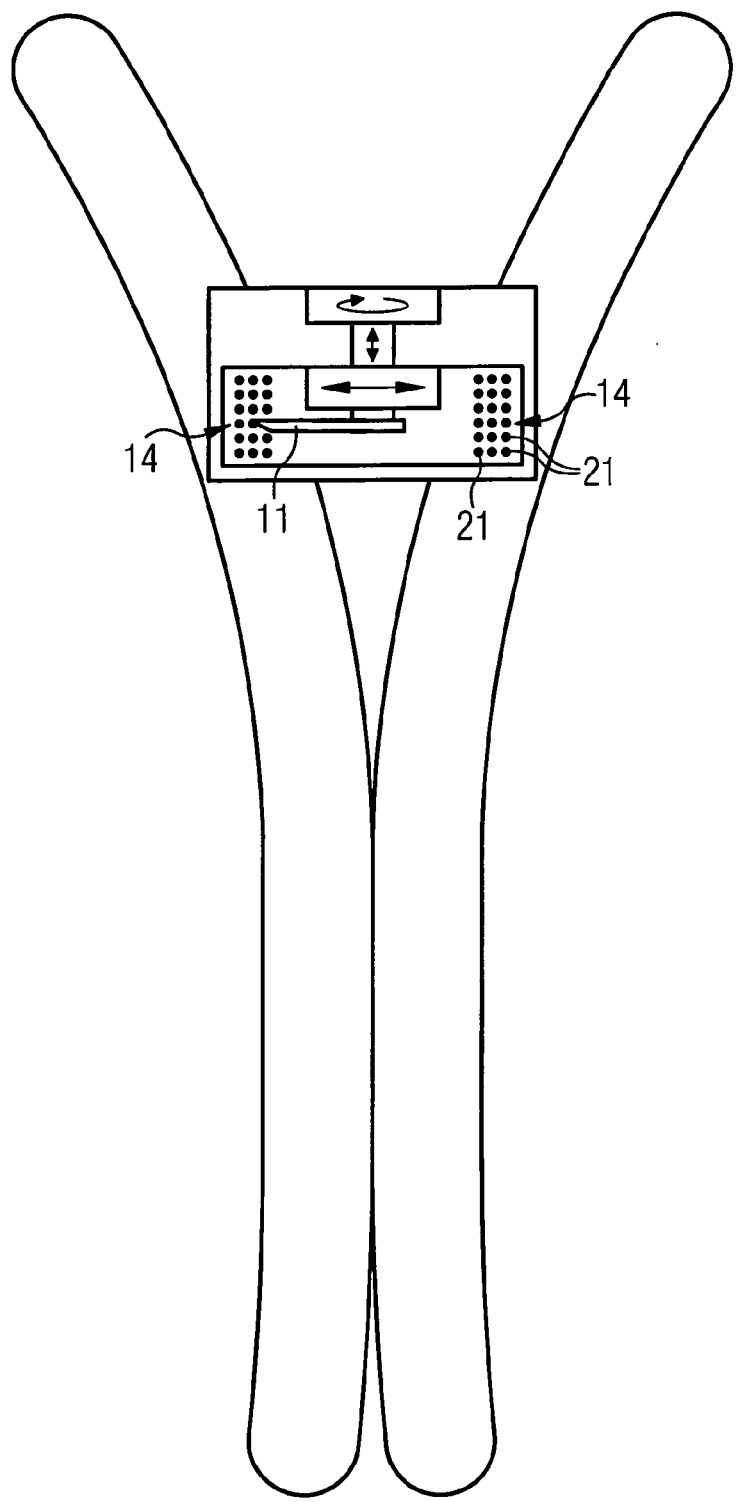
FIG. 13 shows a sixth embodiment similar to the fifth embodiment, but with more steps for laterally displacing the tip end of the infusion needle.

FIG. 13 shows a sixth embodiment similar to the fifth embodiment shown in FIG. 12. In contrast to FIG. 12, the tip end of the infusion needle 11 is not only laterally displaceable between different penetration sites 21 within the same penetration area 14 in a direction perpendicular to the direction of lateral displacement between the two penetration areas 14, but is also laterally displaceable within the same penetration area 14 in a direction parallel to the direction of lateral displacement between the different penetration areas 14. In other words, the tip end of the infusion needle 11 is laterally displaceable in two dimensions within the same penetration area 14.

Figure 14:
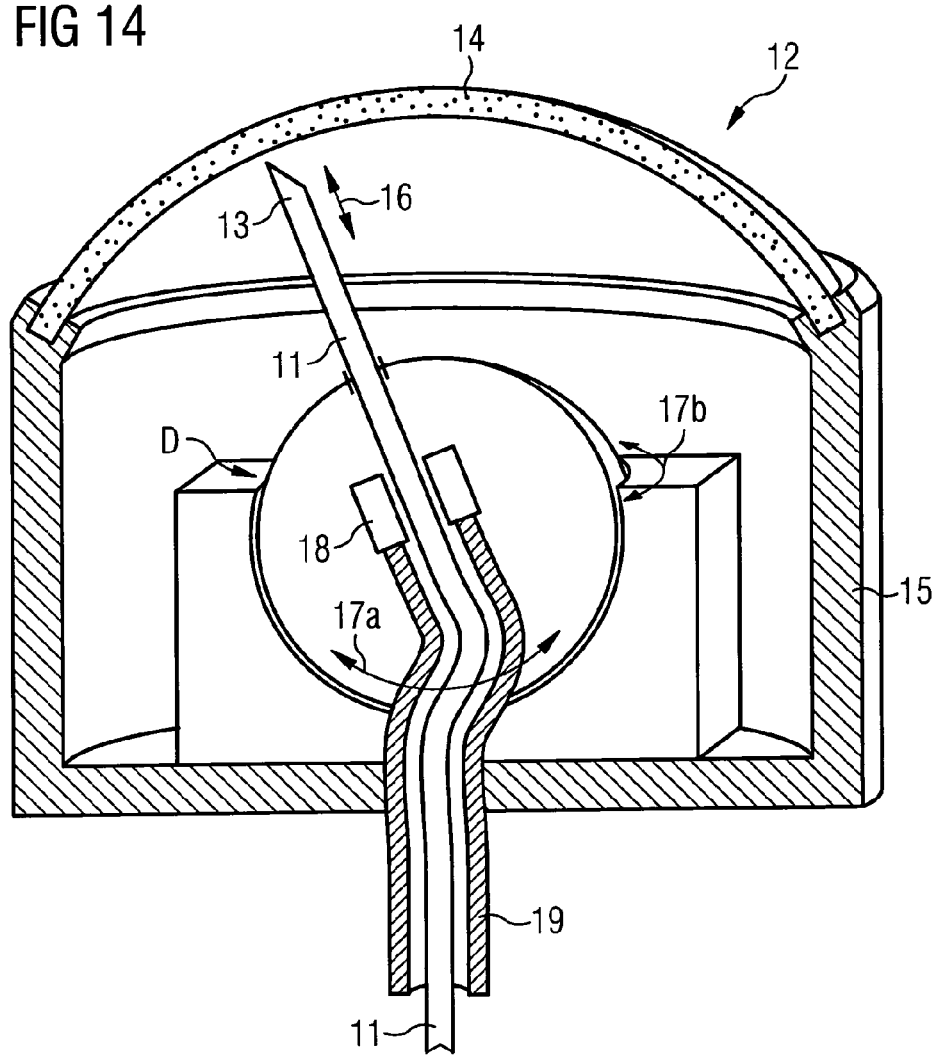
FIG. 14 shows a seventh, spherical embodiment for obtaining a three-dimensional array of penetration sites.

FIG. 14 shows a seventh embodiment which enables the tip end of the infusion needle 11 to be moved along a three-dimensional, spherically curved array of penetration sites. In this embodiment, a part of the first housing 12, more specifically the window area 14, is spherically curved and the front part of the infusion needle 11 is mounted in a sphere so that upon rotation of the sphere along the directions 17a and 17b the tip end 13 of the needle 11 can be moved to any position in front of the window area 14. Once an appropriate position has been adjusted for the tip end 13, the needle 11 can be advanced on the slide 18 so as to penetrate the window area 14. Instead of accommodating the slide inside the sphere, it may likewise be mounted on the outer surface of the sphere. Similarly, the infusion needle 11 itself can be mounted on the outer surface of the sphere. The mechanism for moving the sphere along the directions 17a, 17b can be of many different types, such as mechanical by means of rollers or magnetic.

Figure 15:
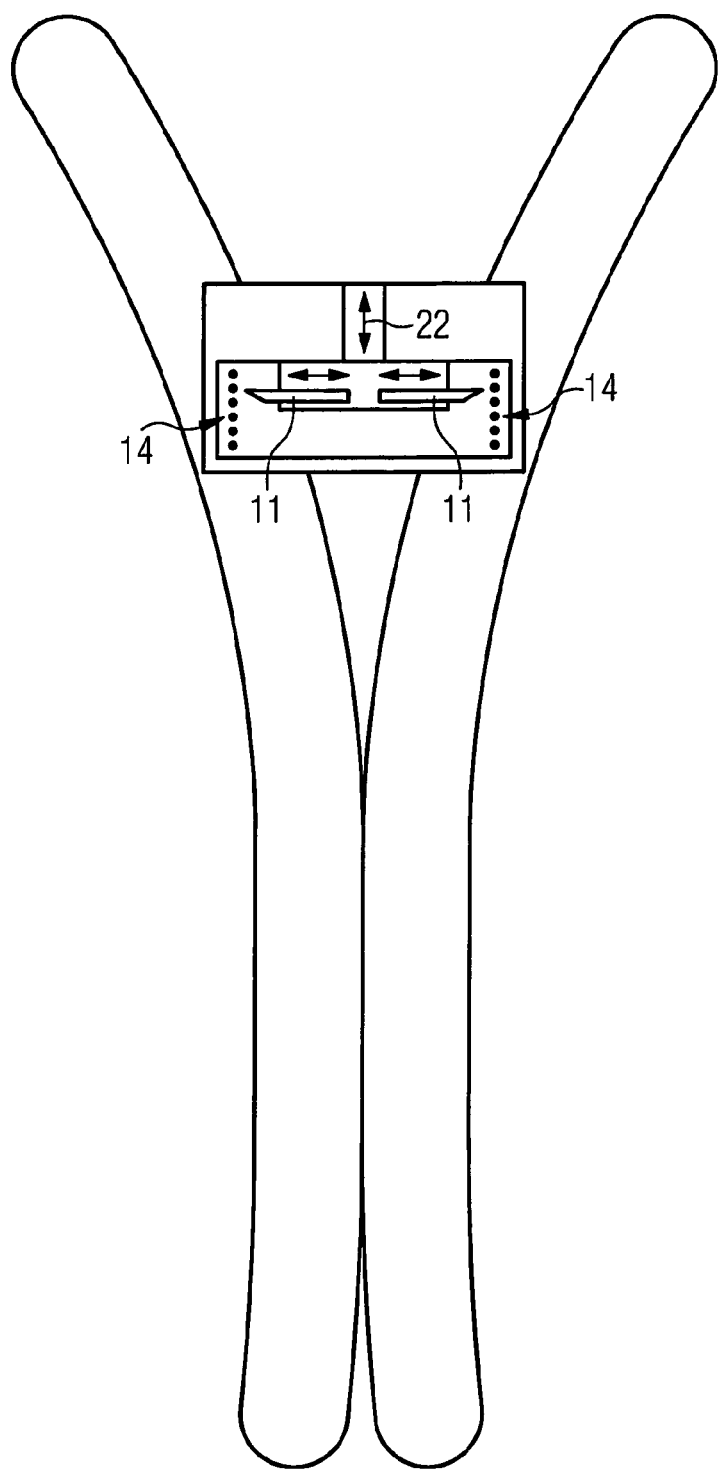
FIG. 15 shows an eighth embodiment comprising the tip ends of two infusion needles in a common housing which are laterally and vertically displaceable.

FIG. 15 shows an eighth embodiment similar to the third embodiment shown in FIG. 5. That is, tip ends of two needles 11 are provided in a common first housing so as to be longitudinally movable in order to advance and retract the tip ends through the penetration areas 14. Instead of mounting the front part of the infusion needles 11 on a turntable 20, as in the embodiment of FIG. 5, so as to change the injection sites 22 within a penetration area 14 upon each injection cycle, the eighth embodiment of FIG. 15 achieves the same result by raising and lowering the tip ends of the two injection needles along a direction 22, similar to the fifth embodiment described above in relation to FIG. 12. Again, the result is that the direction of lateral displacement of the tip ends of the two infusion needles 11 within each of the two different penetration areas 14 is perpendicular to the direction of distance between the two different penetration areas 14. Of course, this embodiment, like the sixth embodiment shown in FIG. 13, can also be modified such that the tip ends of the two infusion needles 11 are laterally displaceable in two dimensions within the same penetration area 14.

FIG. 16 shows a ninth embodiment with a principle of advancing and retracting the infusion needle 11 by means of a pull wire 101. The pull wire 101 is redirected about a pin 102 such that by pulling the wire 101 at an end remotely located somewhere in the patient's body the tip end of the infusion needle 11 will be advanced through the window of the housing 12. A helical spring provides a counterforce so that the infusion needle 11 will be retracted once the pulling force on the pull wire 101 is released. This principle can be combined with other embodiments described hereinbefore and hereinafter. Instead of the helical spring 104, a second pull wire may be provided to retract the infusion needle 11. It is even possible to use a single pull wire 101 running around two pins 102 in a loop, so that pulling the wire 101 in the one direction or in the other direction will cause advancement or retraction of the infusion needle 11.

The pull wire 101 and the infusion needle are guided in a common sheath 103. The common sheath 103 has various functions. First, it gives support to the pull wire 101 in bending sections. Second, it facilitates implantation of the infusion needle 11 along with the pull wire 101. Third, it protects the pull wire 101 against any build-up of fibrosis.

FIG. 17 shows a tenth embodiment which involves remotely actuated pull wires 105, 106 guided within a common sheath 103 along with the infusion needle 11. The pull wires 105 and 106 are directly attached to the front end of the infusion needle 11 on opposite sides thereof so that the tip end of the infusion needle 11 which is mounted on a turntable 20 will be laterally displaced in the one direction or in the other direction depending on whether the wire 105 or the wire 106 is pulled. Instead of using two wires 105, 106, one of the wires may be replaced with a pretensioning means, such as the helical spring 104 in FIG. 16. In addition, a further wire, in particular third wire (not shown), may be provided for lateral displacement of the infusion needle 11 in a further direction, so that a two-dimensional lateral displacement can be achieved by pulling the appropriate wires. In particular, due to the fact that the infusion needle 11 is long and flexibly bendable, one can dispense with the turntable 20 and achieve accurate lateral displacement of the tip end of the infusion needle 11 by pulling the appropriate one of three pull wires which are attached either directly or indirectly to the circumference of the front end of the infusion needle at regularly spaced intervals.

The pull wires may alternatively be attached to an element other than the infusion needle 11, provided that the infusion needle 11 is connected to such other element, so that when the other element is moved or turned by pulling one or more of the wires the tip end of the infusion needle 11 will be displaced accordingly.

FIG. 18 shows an eleventh embodiment with a different principle of advancing and retracting the tip end of the infusion needle, on the one hand, and laterally displacing the tip end of the infusion needle 11, on the other hand. Instead of pull wires, rotating shafts 107, 108 are provided. The drive for driving the rotating shafts 107, 108 is remotely located somewhere in the patient's body. The front ends of the rotating shafts have a threading 109, 110, e.g. in the form of a worm screw, meshing with the teeth of a rack 111, 112 formed either directly or indirectly on the infusion needle 11 and on the turntable 20, respectively. Thus, by turning the rotating shaft 107, the infusion needle 11 will advance or retract, as the case may be, due to the cooperation of the worm screw 109 and the rack 111. The gearing 109, 111 may likewise be arranged remote from the first housing, i.e. within the second housing accommodating the respective other end of the needle. Similarly, by turning the rotating shaft 108, the infusion needle 11 will be displaced laterally in the one or the other direction due to the cooperation of the worm screw 110 and the rack 112 of the turntable 20. Again, the rotating shafts 107, 108 are guided in a common sheath 103 along with the infusion needle 11.

In FIGS. 17 and 18, the action of the pull wires 105, 106 and the rotating shaft 108 make it possible to laterally displace the tip end of the infusion needle 11 between two different penetration areas and/or from a first penetration site to a second penetration site within a single penetration area.

Figure 19:
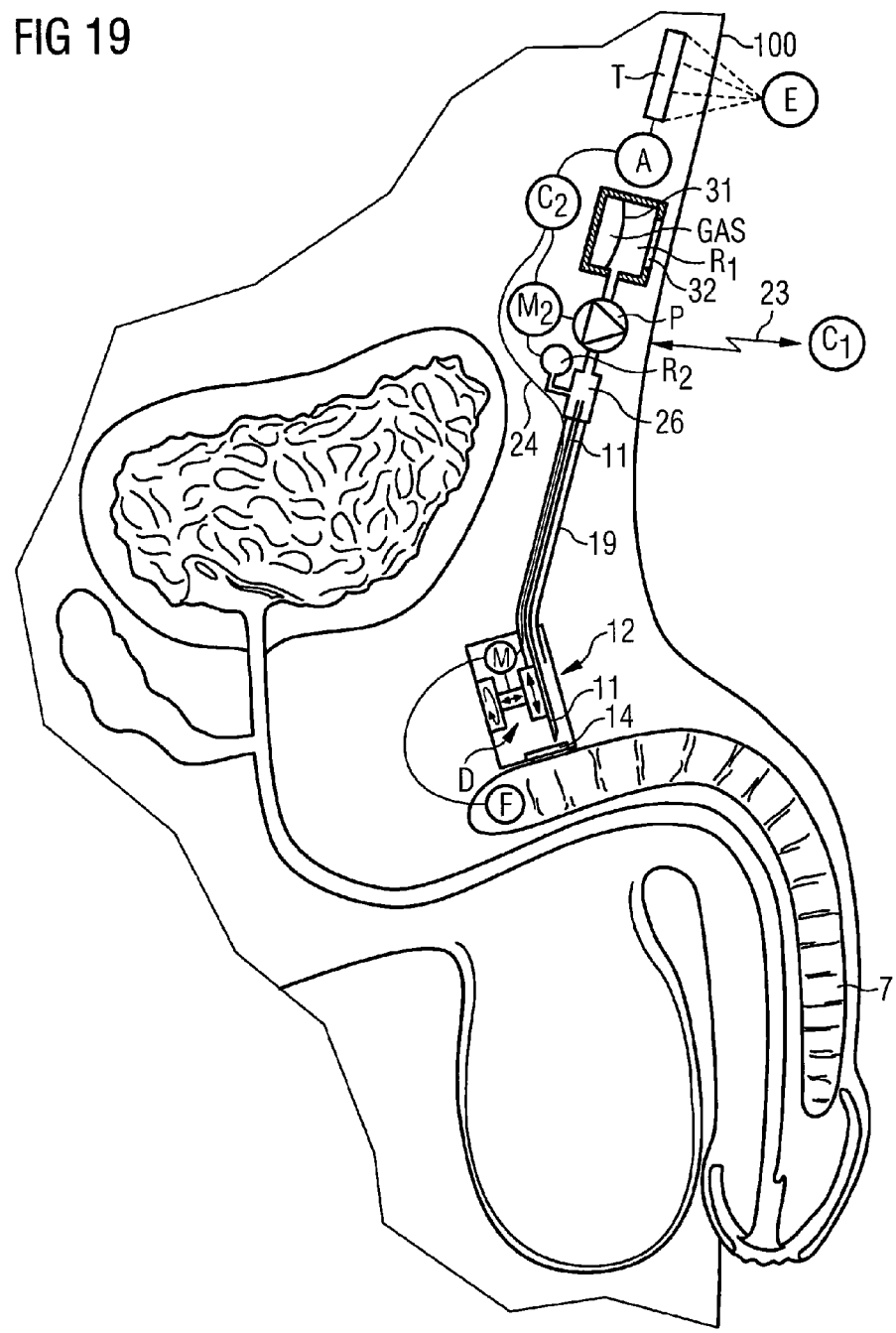
FIG. 19 shows the overall system of the invention implanted in a patient's body according to a first variation.

FIG. 19 shows a first variation of an overall system comprising any one of the first to eleventh embodiments described above. Specifically shown in the variation shown in FIG. 19 is a first housing 12 accommodating the tip end of a single infusion needle 11 and a drive unit D as described in relation to FIG. 12. The housing 12 is implanted with its window areas 14 positioned adjacent the corpora cavernosa 6, 7, of which window areas 14 only one is shown in FIG. 19. A motor M is contained in the housing 12 for driving the drive unit D. While the motor M in the housing 12 may be designed to move the front end of the infusion needle 11 in all directions as indicated in FIG. 19, it is possible and even preferable to cause advancement and retraction of the front end of the infusion needle by advancing and retracting the entire infusion needle from its rear end using an additional motor, so as to minimize the motor size in the housing 12 for reasons of space constraints in the injection area. The additional motor may be accommodated in a separate second housing—not shown in FIG. 19—along with the rear end of the infusion needle and possibly along with further components remotely implanted in the patient's body. The motor M within the housing 12 (and likewise the afore-mentioned additional motor) is controlled by means of a control unit $C_2$ constituting the implantable part of a control system which further comprises an external data processing device $C_1$ by which commands and any other kind of data can be sent to the control unit $C_2$. For instance, the external data processing device $C_1$ may be used to initiate an injection cycle from outside the patient's body, this being done wirelessly as indicated by arrow 23. The implanted control unit $C_2$ not only controls the motor M inside the housing 12 but also controls the energy supply from an accumulator A to the motor M inside the housing 12.

The external data processing device $C_1$ may likewise be used to program the implanted control unit $C_2$. Also, a data transfer port for transferring data between the external data processing device $C_1$ and the implanted control unit $C_2$ may be adapted to transfer data in both directions.

A feedback sensor F implanted inside the patient's penis is shown here as being connected to the motor M inside the housing 12 and may likewise be connected to the implantable control unit $C_2$. The feedback sensor F can sense one or more physical parameters of the patient, such as the drug level inside the corpora cavernosa, the flow volume through the corpora cavernosa, the pressure inside the corpora cavernosa and the like. Other feedback sensors may be provided at a different location so as to sense process parameters of the system, such as electrical parameters, distention, distance and the like.

The conduit 19 guides the infusion needle 11 from a reservoir comprising compartments $R_1$ and $R_2$ and accommodates the wiring 24 for transmitting electric energy from the energy source A to the motor M inside the housing 12.

In the variation of the entire system shown in FIG. 19, the reservoir comprises a first compartment $R_1$ with e.g. a saline solution included therein, and a second compartment $R_2$ with e.g. a drug in powder form or freeze-dried form included therein. A pump P driven by a second motor $M_2$ is arranged to pump infusion liquid from the reservoir $R_1$ to the infusion needle 11. The infusion liquid pumped by the pump P will pass through a mixing chamber 26 into which drugs will be released from the reservoir $R_2$ in appropriate time coordination. The motor $M_2$ or a different motor may cause the drugs to be released from the second reservoir $R_2$. The motor $M_2$ is also controlled by the control unit $C_2$. Thus, infusion liquid pumped via the pump P from the relatively large first reservoir $R_1$ through the mixing chamber 26, in which it is mixed with the drugs released from the second reservoir $R_2$, will reach the infusion needle 11 which has meanwhile penetrated the self-sealing window area 14 of the housing 12 and will flow into the corpus cavernosum 7.

In addition to or instead of the control unit $C_2$, a pressure sensitive switch for activating the motor M inside the housing 12 and/or the motor $M_2$ may be arranged subcutaneously.

Although the embodiment shown in FIG. 19 may comprise one of a great variety of reservoir types, a particular reservoir type will now be described. The volume of the reservoir $R_1$ is divided into two sections by means of a membrane 31. One section is filled with gas whereas the other section is filled with the infusion liquid (saline solution). An infusion port 32 allows for refilling the reservoir $R_1$ with infusion liquid by means of a replenishing needle. When the reservoir $R_1$ is in its full state, the gas section is at ambient pressure or overpressurized. As infusion liquid is drawn from the reservoir $R_1$ by means of the pump P upon each infusion cycle, the pressure in the gas section will decrease below ambient pressure, i.e. to a negative relative value. Depending upon the particular type of pump P, it may be advantageous to provide a single acting ball valve to prevent any backflow from the pump P to the reservoir $R_1$.

There are various ways of providing the motors M and $M_2$ with energy. In the variation shown in FIG. 19, energy is supplied from outside the patient's body either for direct use by the motors and/or for charging the accumulator A, which may be in the form of a rechargeable battery and/or a capacitor. An extracorporal primary energy source E transmits energy of a first form through the patient's skin 100 to an energy transforming device T which transforms the energy of the first form into energy of a second form, such as electric energy. The electric energy is used to recharge the accumulator A which provides secondary energy to the motor M upon demand.

The external primary energy source E may be adapted to create an external field, such as an electromagnetic field, magnetic field or electrical field, or create a wave signal, such as an electromagnetic wave or sound wave signal. For instance, the energy transforming device T as shown in FIG. 19 may act as a solar cell, but adapted to the particular type of wave signal of the primary energy source E. The energy transforming device T may also be adapted to transform temperature changes into electrical energy.

Instead of the external primary energy source E, an implantable primary energy source E may be used, such as a regular long-life battery instead of the accumulator A.

The energy signal may also be used to transmit signals from the external data processing device $C_1$ by appropriate modulation of the energy signal, regardless of whether the energy is transmitted wirelessly or by wire, the energy signal thereby serving as a carrier wave signal for the digital or analog control signal. More particularly, the control signal may be a frequency, phase and/or amplitude modulated signal.

Figure 20:
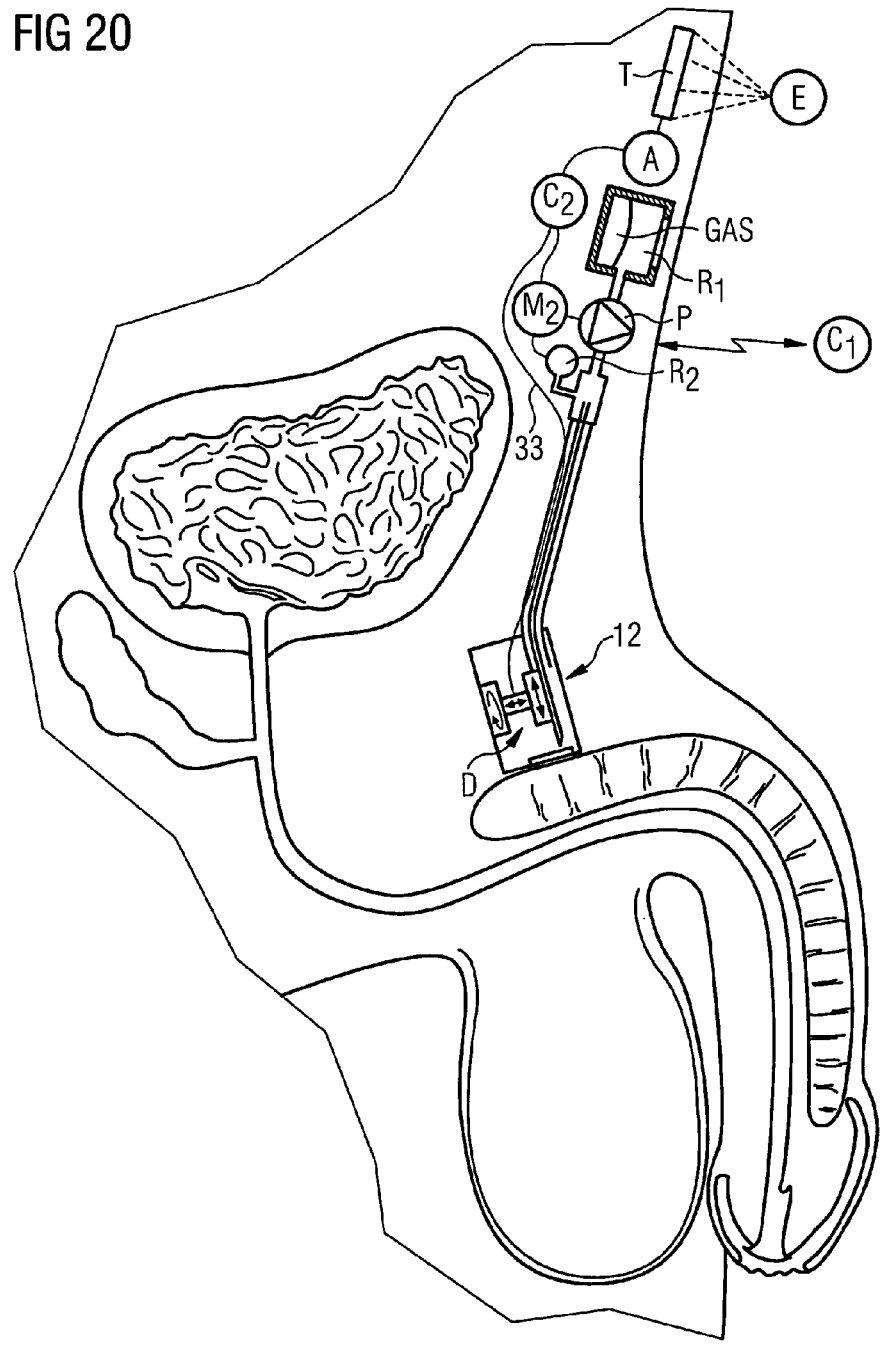
FIG. 20 shows the overall system of the invention implanted in the patient's body according to a second variation.

FIG. 20 shows a second variation of the entire system which basically differs from the system of FIG. 19 only in that the motor M inside the housing 12 is dispensed with. Instead, the motor $M_2$ is used to drive the drive unit D. This is achieved by means of a rotating shaft 33 in the form of an elastically bendable worm screw, the rotating shaft 30 replacing the wiring 24 of the system shown in FIG. 19. Alternatively, since the infusion needle 11 is long and flexible, the infusion needle may be advanced by engagement of two helical gears, one of which is formed on the rear end of the infusion needle, or by a similar gearing cooperating with the infusion needle's rear end.

Figure 21:
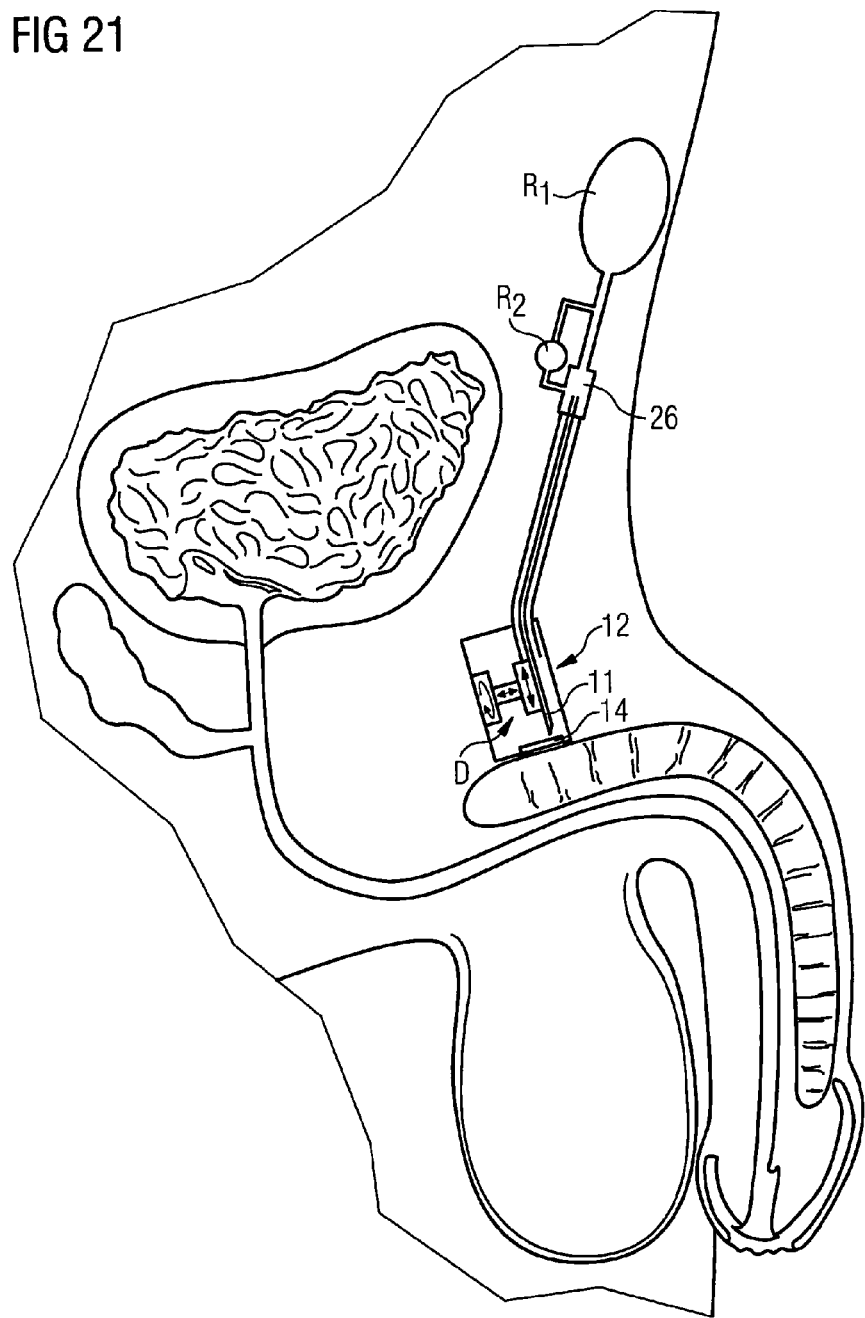
FIG. 21 shows the overall system of the invention implanted in the patient's body according to a third variation.

FIG. 21 shows a third variation of the entire system which operates purely mechanically. The reservoir $R_1$ containing the infusion liquid, i.e. the saline solution, is of balloon type, thereby functioning both as a reservoir and as a pump if it is compressed manually from outside the patient's body. The pressure generated in the reservoir $R_1$ will act on the reservoir $R_2$ containing the drug. Upon a certain pressure, the drug will be released from the reservoir $R_2$ into the mixing chamber 26 and upon further increase of the pressure the infusion liquid will be allowed to enter the mixing chamber 26, mix with the drug released from the reservoir $R_2$, flow towards the infusion needle 11, and build up pressure on the infusion needle 11 such that the drive unit D is caused to advance the infusion needle 11 through the self-sealing window area 14 into the patient's corpus cavernosum. Once the pressure is released, the infusion needle 11 will retract automatically due to mechanical spring forces or the like and move into a different position in which it can penetrate the second of the two self-sealing window areas 14 when the reservoir $R_1$ is compressed again. Where two infusion needles 11 are provided, a single compressing action on the reservoir $R_1$ would be sufficient to inject the drug into both the left and right corpora cavernosa.

Figure 22:
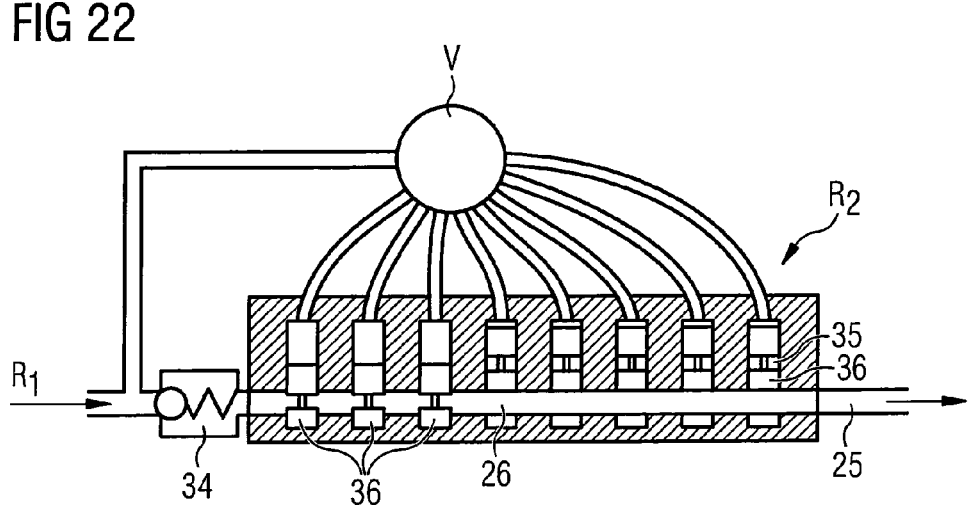
FIG. 22 shows drug compartments as part of the reservoir of the system according to a first principle.

FIG. 22 shows a first principle of how drugs within a plurality of compartments 34 of the reservoir $R_2$ can be released one at a time by a purely hydromechanical solution. As the infusion liquid is urged from the reservoir $R_1$ towards the conduit 25 leading to the infusion needle or needles, it is first blocked by a spring-loaded ball valve 34 which opens only when a certain pressure is exceeded. The pressure building up in front of the ball valve 34 is guided by means of a stepper valve V sequentially onto one of a plurality of compartments 35. The compartments are each formed as a cavity 35 within a piston 36. Once a certain pressure is exceeded, the piston 36 will be pushed into a position where the compartment 35 is in flow communication with a mixing chamber 26. In the state shown in FIG. 22, three pistons 36 have already been pushed into such position. When the pressure in the reservoir $R_1$ is further increased, the spring force of the ball valve 34 will be overcome and the infusion liquid urged from the reservoir $R_1$ towards the conduit 25 will take with it the drug that has been released into the mixing chamber 26.

Figure 23:
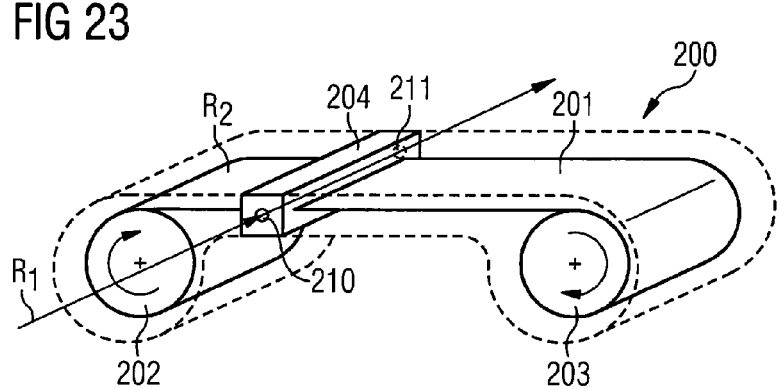
FIG. 23 shows drug compartments mounted on a tape wound on a reel in a replaceable cassette as part of the reservoir of the system according to a second principle.
Figure 24:
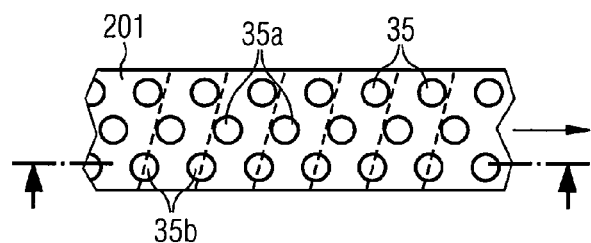
FIG. 24 shows a part of the tape of FIG. 19 in greater detail.
Figure 25:
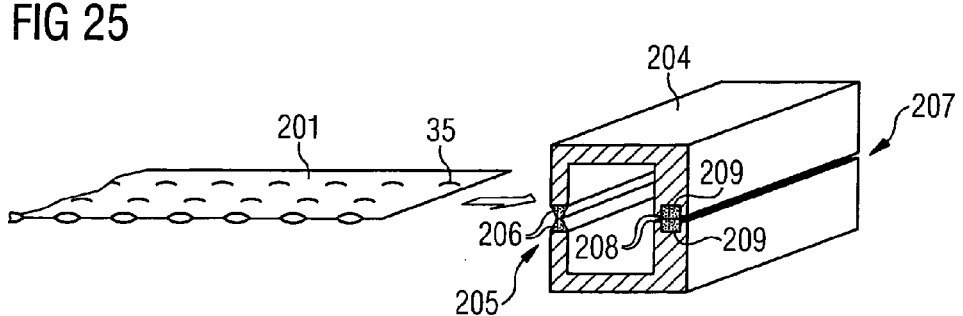
FIG. 25 shows the principle of operation of the replaceable cassette of FIG. 23.

FIGS. 23 to 25 show a second principle of realizing the reservoir $R_2$ comprising a plurality of small drug compartments 35, 35a, 35b. The drug compartments are integrally formed in a tape 201 which is wound on a first reel 202 and can be unwound from said first reel 202 onto a second reel 203. The reels 202, 203 and the tape 201 are contained in a cassette 200 which may be inserted in the entire system so as to form part of the reservoir. The cassette 200 is preferably replaceable.

As can be seen in FIG. 24, the compartments 35, 35a, 35b containing the drug e.g. in powder form or freeze-dried form are arranged in a plurality of rows as seen in the transporting direction (indicated by the arrow). However, the compartments 35 of one row are a certain distance offset in the transporting direction from the compartments 35a and 35b of the other rows. Thus, when the tape 201 is wound from reel 202 to reel 203, it is guided through a conduit 204 forming part of the cassette 200 through which the infusion liquid is pumped from the reservoir $R_1$ to the infusion needle or needles, and the compartments 35, 35a, 35b will enter the conduit 204 one after the other.

While it is conceivable to open one of the compartments 35, 35a, 35b that has entered the conduit 204 by mechanical action, such as a hammer or piercing element, the opening of the compartments 35 in the embodiment shown in FIGS. 23 to 25 needs no further action other than winding the tape 201 onto the reel 203. That is, as can be seen from FIG. 25, when the tape 201 enters the conduit 204 through a first slit 205, the compartments 35 will not be damaged due to the fact that the slit 205 is relatively wide and is closed by two soft sealing lips 206. However, when the tape 201 exits the conduit 204 on the other side thereof, it will have to pass a narrower second slit 207 with front edges 208 that are not resilient. The compartments 35 will therefore burst on their way out of the conduit 204 when they slip between the edges 208 of the narrow slit 207. Soft seals 209 in the slit 207 prevent liquid from leaking from the conduit 204.

The entry 210 and the exit 211 of the conduit 204 within the cassette 200 each include a valve that automatically closes when the cassette 200 is removed from the system and automatically opens when the cassette 200 is installed in the system. This allows for replacement of the cassette 200 without adversely affecting the remaining components of the overall system.

Figure 26:
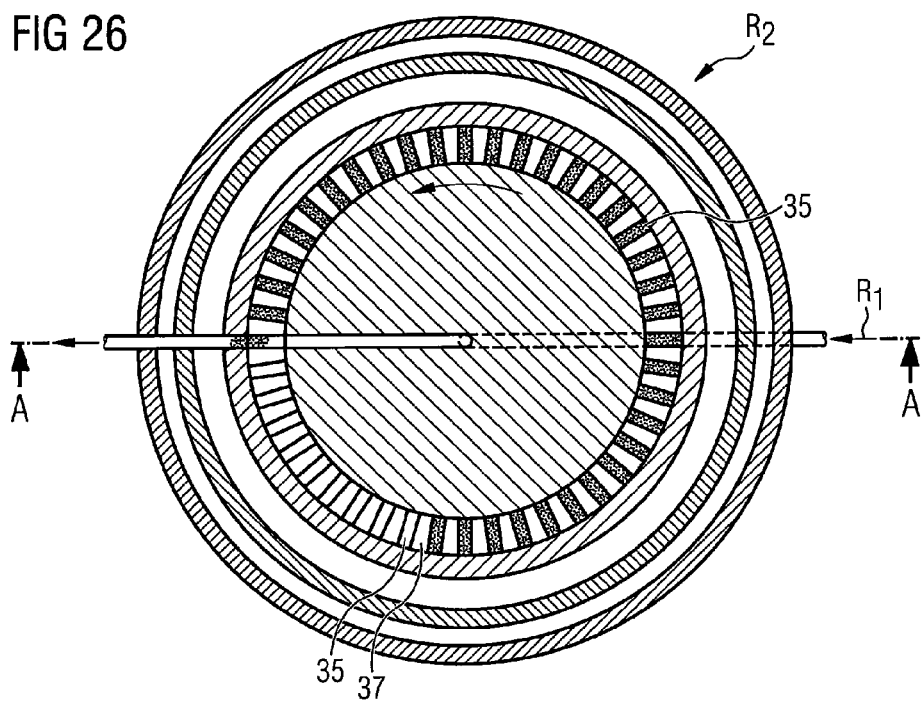
FIG. 26 shows drug compartments as part of the reservoir of the system according to a third principle.
Figure 27:
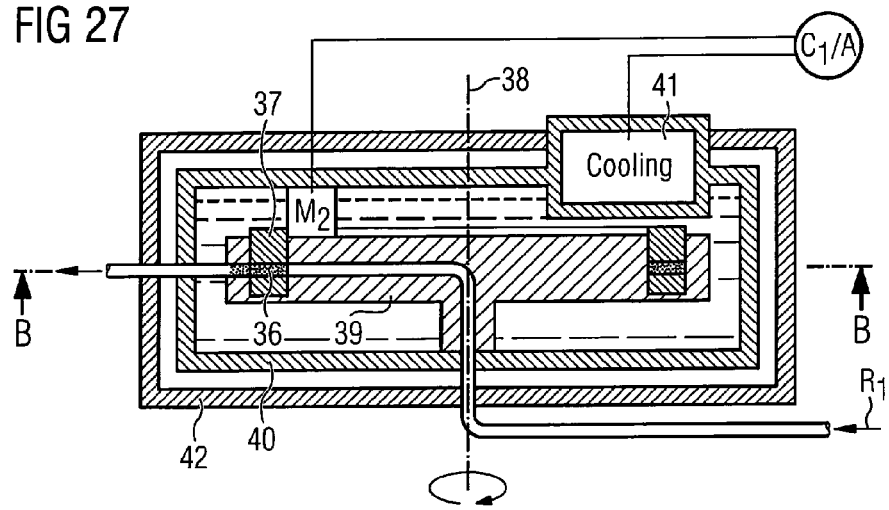
FIG. 27 shows a cross-sectional view through the drug compartments of FIG. 26 including an insulation chamber and cooling device.

FIGS. 26 and 27 show a third principle of realizing the reservoir $R_2$ comprising a plurality of small drug compartments 35. While FIG. 26 shows a cross-sectional plan view according to section BB in FIG. 27, FIG. 27 shows a cross-sectional side view thereof according to section AA in FIG. 26. The compartments 35 containing the drug in powder form or freeze-dried form are arranged in a rotatable plate 37. A motor $M_2$ is provided to rotate the plate 37 about an axis 38. The motor $M_2$ is controlled to advance the plate 37 stepwise so as to bring one compartment 35 at a time in line with the conduit 39 connecting the reservoir $R_1$ containing the saline solution with the infusion needle or needles. Energy is supplied to the motor $M_2$ from the accumulator A via the control unit $C_1$.

The rotatable plate 37 is mounted in a fixed base plate 39 which itself is fixedly mounted in a housing 40 insulating the base plate 39 and the rotatable plate 37 thermally against an outer housing 42. A cooling device 41 is provided to cool a liquid surrounding the base plate 39 and rotatable plate 37 down to a temperature below 37° C. This serves to protect the drugs inside the compartment 36 from degrading too quickly. The accumulator A supplies the cooling device 41 with energy.

Figure 28:
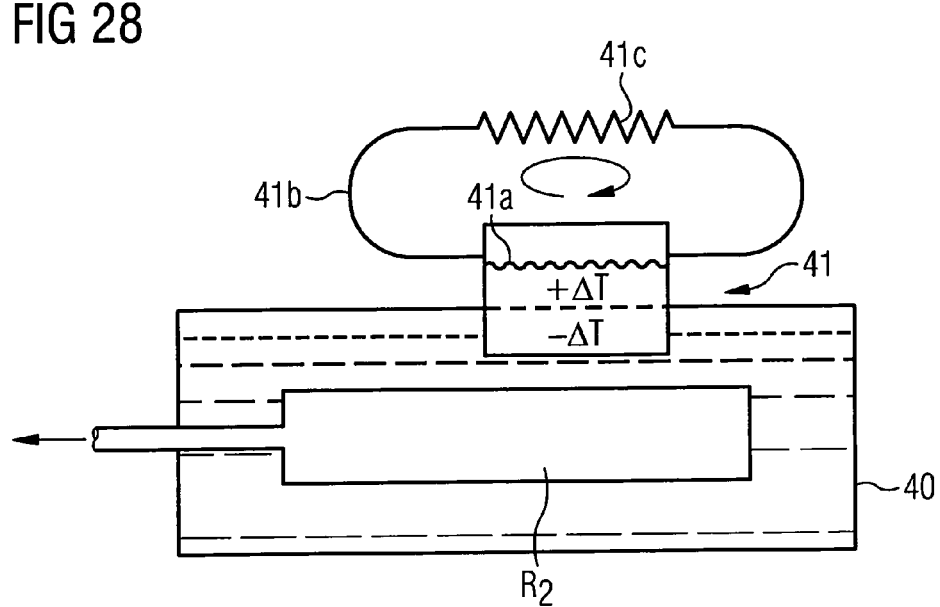
FIG. 28 shows the principle of the cooling device of FIG. 27 in combination with a heat exchanger.

FIG. 28 shows a general principle of cooling the reservoir $R_2$ containing the drug to be cooled. The cooling device 41 may be an electrothermal cooler, i.e. based on the Peltier effect consuming electric energy, or may be of the refrigerator type. Accordingly, the cold part of the cooler 41 is placed on the side to be cooled whereas the warm part of the cooling device 41 is placed on the other side so that the heat energy can be dissipated to the outside. An increased surface 41a on the warm side of the cooling device 41 serves to increase heat dissipation. Furthermore, a heat exchanging fluid may be passed through a conduit 41b along the increased surface 41a to transfer the dissipated heat energy to a remote location within the patient's body where the heat is dissipated into the patient's body through a specific heat exchanging surface 41c.

Figure 29:
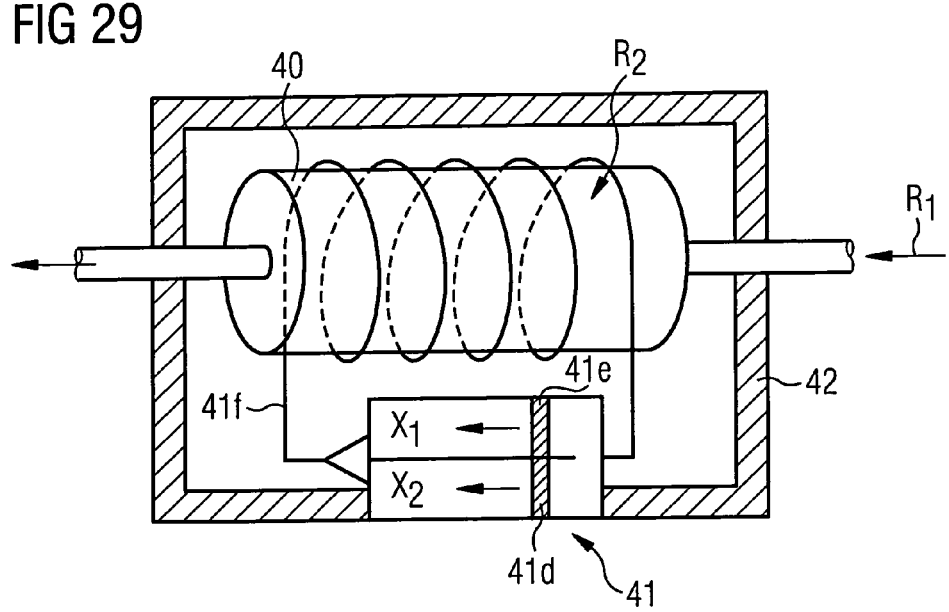
FIG. 29 shows a specific embodiment for the cooling device of FIG. 27.

FIG. 29 shows a different principle of cooling the drugs contained in the reservoir $R_2$. In this embodiment, two chemicals X1 and X2 are contained separate from each other in respective compartments of the cooling device 41. When the chemicals X1 and X2 are brought together, they will react with each other and such reaction will consume energy which is absorbed as thermal energy from the surroundings. By means of two pistons 41d, 41e, the chemicals X1, X2 are dispensed into a cooling line 41f in a controlled manner, which cooling line is preferably in contact with the housing 40 containing the reservoir $R_2$. The chemical mixture X1-X2 displaced within the cooling line 41f will flow back into the chamber containing the chemicals X1, X2, but onto the other side of the pistons 41d, 41e.

Figure 30:
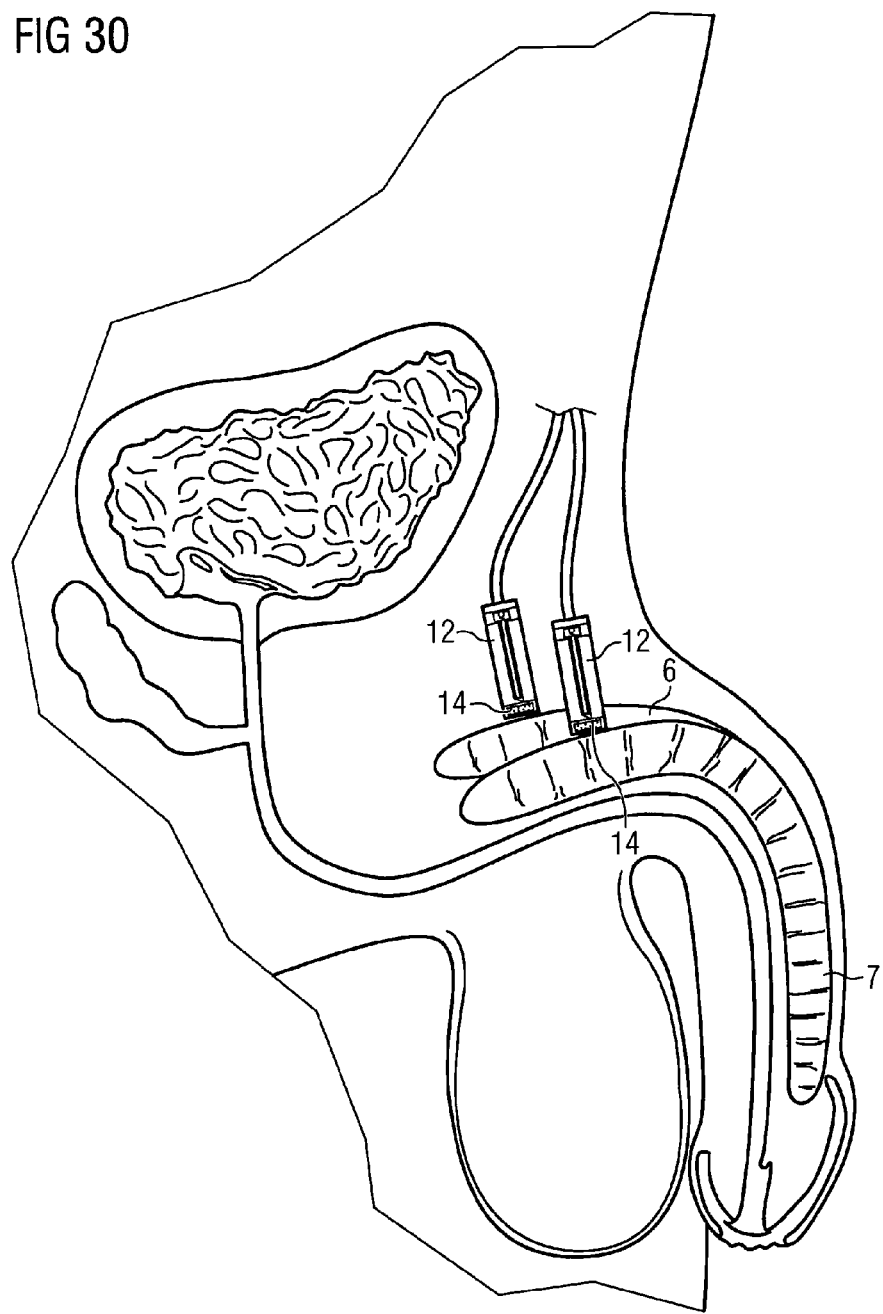
FIG. 30 shows a part of the system implanted in the patient's body comprising separate infusion needles for the right and the left corpus cavernosum, FIG. 31 diagrammatically shows the system of FIG. 30.
Figure 31:
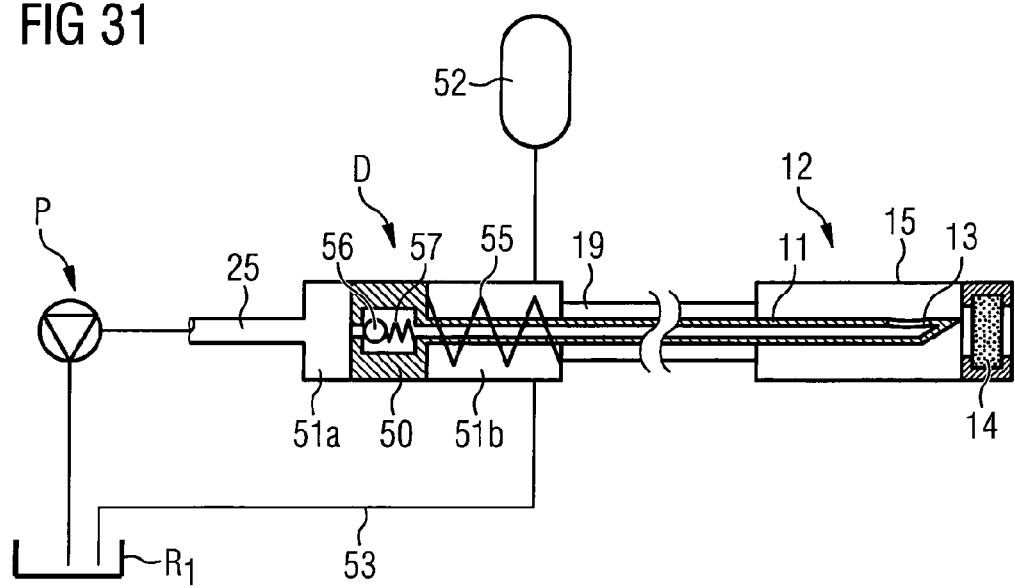

A further embodiment is shown in FIG. 30. In this embodiment, again, two separate long and flexible infusion needles 11 are provided with their respective front ends accommodated in a housing 12, one infusion needle for each of the left and right corpora cavernosa. However, unlike the previously discussed embodiments, the two needles each have their own housing 12 implanted in the patient's body with their respective self-sealing window area 14 adjacent the left and right corpora cavernosa, respectively. This principle is shown in FIG. 31 in more detail with respect to one of the two needles. The drive unit D comprises a piston 50, to which the hollow infusion needle 11 is attached. The piston 50 separates a first chamber 51a in front of the piston 50 and a second chamber 51b behind the piston 50. While the pressure in the first chamber 51a corresponds to the pressure exerted by the pump P via the conduit 25, the pressure in the second chamber 51b can be kept at a lower value. The second chamber 51b may be filled with a liquid, such as the infusion liquid, and the liquid may be urged into a flexible volume 52. The flexible volume 52 could be of simple balloon type so as to fill up without exerting any strong counterforce.

Instead of the flexible volume 52, a conduit 53 may connect the second chamber 51b with the reservoir $R_1$. Thus, when the needle 11 is advanced, liquid will be dispelled from the second chamber 51b through the conduit 53 into the reservoir and as the needle 11 is retracted by means of a return spring 55, liquid will be drawn from the reservoir $R_1$ through the conduit 53 back into the second chamber 51b.

The injection process is carried out as follows. As the pressure is increased in the first chamber 51a by means of the pump P remote from the housing 12 accommodating the tip end 13 of the infusion needle 11, the entire infusion needle 11 which is guided in the conduit 19 will be displaced against the force of the spring 55 of the drive unit B. Thus, the tip end 13 of the infusion needle 11 will penetrate through the self-sealing window area 14 press-fitted into the wall 15 of the housing 12 and will further penetrate any fibrosis having built up in front of the housing. When the return spring 55 is completely compressed and the pressure built up by the pump P is further increased, a ball valve 56 will be displaced against a second return spring 57 which is stronger than the first return spring 55. That way, as long as the pressure is held at a sufficiently high level, infusion liquid will be pumped from the reservoir $R_1$ through the conduit 25, the hollow infusion needle 11 and the needle's laterally arranged exit port into the patient's body. Upon pressure release, the ball valve 56 will close due to the return springs 55 and 57, and then the needle 11 will be retracted to its initial position shown in FIG. 22.

Figure 32:
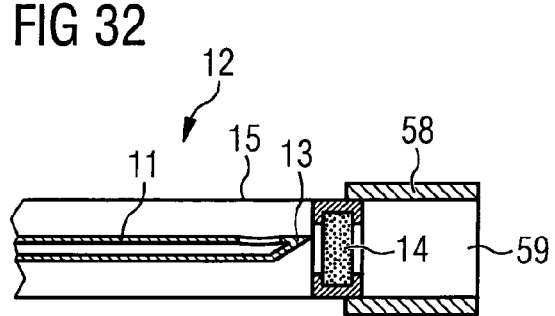
FIG. 32 shows a part of the system of FIG. 31, including a tube into which the tip end of the infusion needle can be advanced.

It may be advantageous not to pierce any living tissue by means of the injection needle 11 once it is advanced through the outer wall 15 of the housing 12. Therefore, as shown in FIG. 32, a tube 58 may be placed in front of the window area 14. The cross sectional form of the tube 58 may be adapted to the cross-sectional form of the window area 14, i.e. where the window area 14 is rectangular, the tube 58 likewise has a rectangular cross-section.

The exit end of the tube 58 has an open area 59 sufficiently large to prevent growth of fibrosis from spanning over the open area. Fibrosis will slowly grow into the tube along the tube's inner surface, before it reaches the window area 14 after a relatively long time. The tip end 13 of the needle 11 will therefore not have to penetrate any fibrosis during the first while after implantation of the system. Preferably, the open area 59 has an opening width of at least 3 mm. The length of the tube 58 may be in the range of 4 mm to 30 mm. The opening width 59 and the length of the tube 58 should be adjusted such that the substance injected into the tube 58 can safely seep into the patient's body. Thus, the longer the tube is, the larger the opening width thereof should be.

Figure 33A:
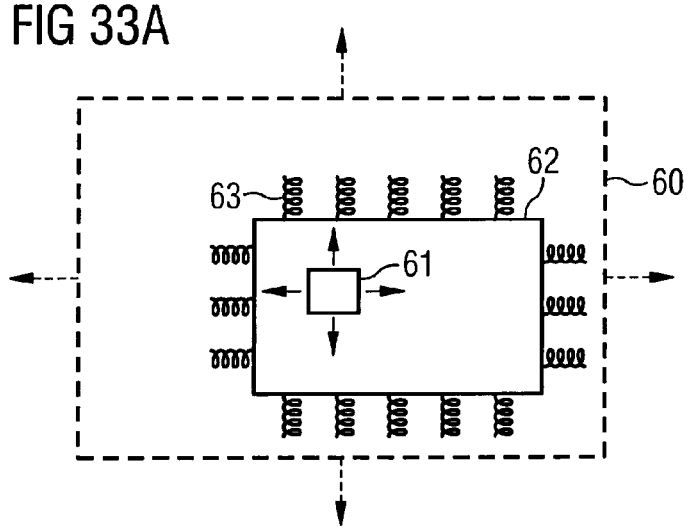
FIGS. 33A to 33C show a first and second embodiment for electromagnetically displacing the tip end of the infusion needle in a plurality of lateral directions.
Figure 33B:
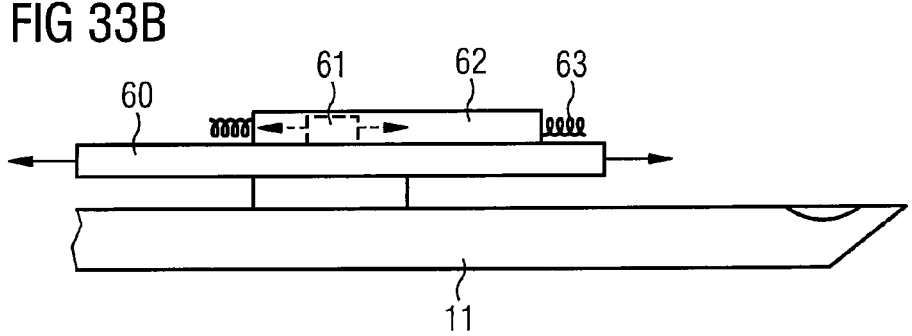

FIGS. 33A and 33B show a first embodiment for displacing the tip end of the infusion needle 11 in two or more different directions, i.e. a two-dimensional displacement. More specifically, FIG. 33A shows a plan view, whereas FIG. 33B shows a side elevational view schematically. As can be seen, a plate 60 to which the infusion needle 11 is fixedly mounted has a projection 61 extending into a frame 62 within which the projection 61 is free to move in any direction. Electromagnetic coils 63 are mounted on the sides of the frame 62 and are individually energizable. The electromagnetic coils 63 constitute the first part of an electromagnetic drive whereas the projection 61 is configured to constitute the second part of the electromagnetic drive. Thus, when one or more of the electromagnetic coils are energized, an electromagnetic field is created in the frame 62 and the electromagnet second part, i.e. the projection 61, will adjust its position within such field accordingly. Due to the fact that the front end of the infusion needle 11 is fixedly mounted to the plate 60, the infusion needle 11 will move along with the projection 61. This way, the tip end of the infusion needle 11 can be displaced laterally and can also be advanced and retracted.

More preferably, however, the infusion needle 11 is attached to the electromagnetic drive in a different manner, namely perpendicular to the plane defined by the electromagnetic coils 63 (rather than in parallel as in FIG. 33B). As a result, the tip end of the infusion needle will be displaceable in a plurality of lateral directions rather than being advanceable and retractable. The drive unit for advancing and retracting the infusion needle 11 is instead preferably connected to the rear end of the long and flexibly needle.

Figure 33C:
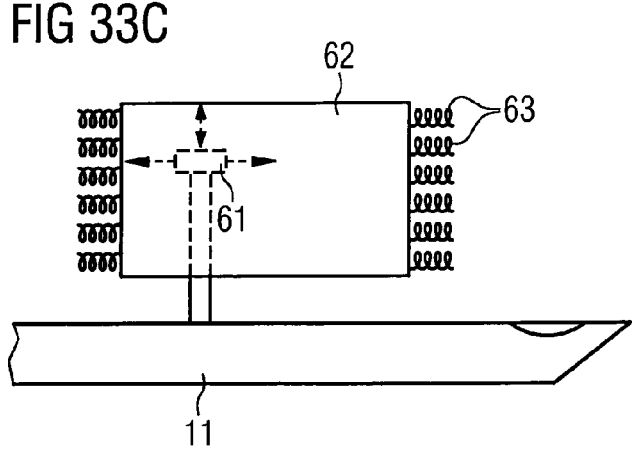

Alternatively, the electromagnetic drive may be such as to displace the tip end of the infusion needle in any lateral direction and, in addition, to advance and retract the infusion needle. This can be achieved e.g. with a structure as schematically shown in FIG. 33C relating to a second embodiment for displacing the tip end of the infusion needle 11. FIG. 33C shows an elevational side view similar to FIG. 33B, but the electromagnetic coils 63 do not define a single plane, but rather a plurality of planes is defined one above the other by providing additional electromagnetic coils 63 in a vertical direction. The top plan view would be similar to FIG. 33A. This way, the electromagnet second part 61 fixedly connected to the needle 11 moves within a three-dimensional frame 62 depending on the energization of respective ones of the magnetic coils 63.

Figure 34A:
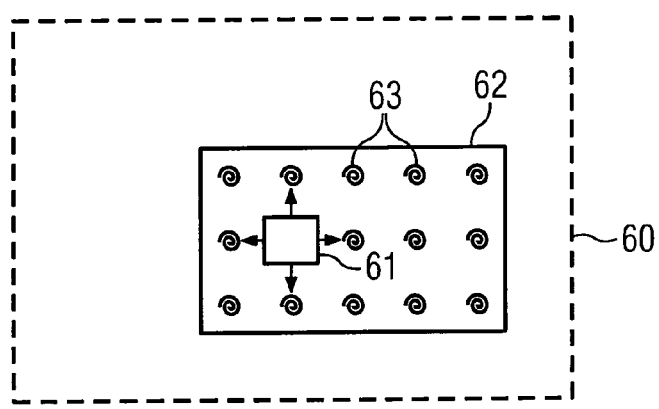
FIGS. 34A and 34B show a third embodiment for electromagnetically displacing the tip end of the infusion needle in a plurality of lateral directions.
Figure 34B:
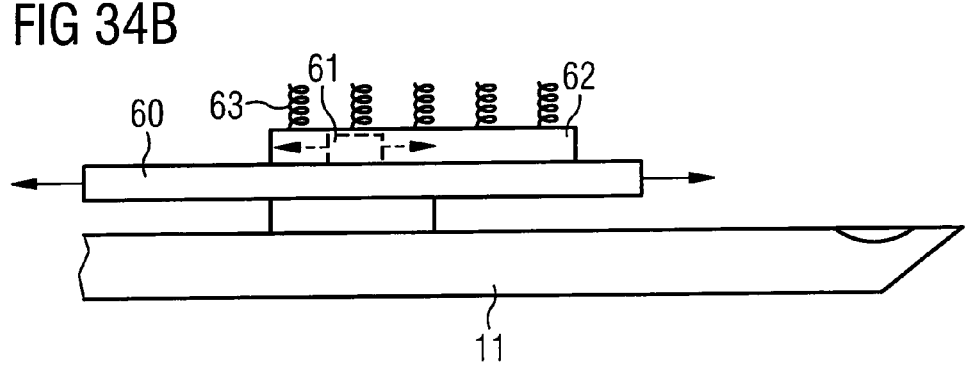

FIGS. 34A and 34B show a plan view and a side view of a third embodiment of an electromagnetic drive for moving the tip end of the infusion needle 11 in a plurality of directions. In this embodiment, the electromagnetic coils 63 constituting the electromagnet first parts are arranged in a first plane and the electromagnet second part constituted by the protrusion 61 fixedly connected to the infusion needle 11 via the plate 60 is movable in a plane in front of or behind the plane defined by the electromagnet first parts. However, the electromagnetic coils 63 are oriented differently in this third embodiment. Again, depending upon the energization of the individual electromagnetic coils, the electromagnet second part, i.e. the protrusion 61, will adjust its position in the created electromagnetic field within the frame 62.

A method of treating a human being (or an animal) by implanting at least part of the system in the patient's body comprises the steps of cutting the skin, dissecting free a first area near the left and right corpus cavernosum, placing the at least one first housing accommodating the tip end or ends of the at least one infusion needle within said dissected area such that the tip end, when penetrating the housing's outer wall, can penetrate into the left and right corpus cavernosum and/or the two deep arteries of the right and left corpus cavernosum and/or into muscle tissue regulating blood flow to the patient's left and right corpus cavernosum and/or into another kind of tissue in close proximity to the patient's left and right corpus cavernosum allowing stimulation of erection of the two corpora cavernosa, placing at least one second housing accommodating the respective other end or ends of the at least one infusion needle within the patient's body remote from the at least one first housing, and finally closing at least the skin after implantation of at least parts of the system.

Where parts of the system are implanted remote from the corpora cavernosa, a second area remote from the first area may be dissected free in order to place e.g. the at least one reservoir in the patient's body at the remote second area, with a conduit connecting the reservoir with the rear end of the at least one infusion needle accommodated in the at least one second housing. In this case, it is preferable to place the second housing and/or the reservoir adjacent the patient's symphyseal bone.

One or more of the following elements may be placed within the patient's body remote from the housing or housings accommodating the at least one needle:
the pump (P),
at least one motor (M, $M_2$) for actuation of the drive unit (D) or a drive driving the drive unit, and/or the pump (P) or any other energy consuming part of the system,
energy storage means (A) for providing the at least one motor with energy,
galvanic coupling elements between either an external energy source (E) or the energy storage means (A) and the motor (M, $M_2$) for transmitting energy to the motor in contacting fashion,
wireless coupling elements adapted to connect either the motor (M, $M_2$) or the energy storage means (A) or both to an extracorporal primary energy source for transmitting energy to either the motor or the energy storage means or both in non-contacting fashion,
control unit (C1) for controlling the motor (M, $M_2$),
a data transmission interface for wirelessly transmitting data from an external data processing device ($C_2$) to the control unit ($C_1$),
the feedback sensor (F),
wireless energy transforming means, and
the injection port (32) for refilling the reservoir ($R_1$).

The invention claimed is:

1. A penis erection stimulation system, comprising at least one flexibly bendable infusion needle with a tip end of each of said at least one infusion needle arranged in at least one first housing for penetrating the first housing's outer wall and having the respective other end arranged in at least one second housing, the first and second housings being adapted for implantation inside the patient's body, wherein the at least one second housing is provided for implantation inside the patient's body remote from the at least one first housing and wherein the injection needle is sufficiently long to bridge the distance from the at least one second housing for remote implantation to the at least one first housing and further through the first housing up to the outer wall of the first housing,
at least one reservoir adapted for implantation inside the patient's body remote from the at least one first housing and in fluid connection with the at least one infusion needle to supply to the infusion needle a substance to be injected into the patient's body, at least one pump adapted for implantation inside the patient's body remote from the at least one first housing and further adapted to advance the substance from the reservoir to the at least one infusion needle, and
at least one drive unit adapted for implantation inside the patient's body, the at least one drive unit being coupled to the at least one infusion needle and arranged at least for advancing and retracting the at least one infusion needle so that the at least one infusion needle penetrates with the tip end or ends thereof at least one penetration area of said at least one first housing's outer wall so as to allow for stimulation of penis erection by injecting the substance through said at least one penetration area via the at least one infusion needle.

2. The system of claim 1, wherein the infusion needle is guided in a sheath between the first and second housings.

3. The system of claim 1, wherein at least a part of the at least one drive unit is adapted for implantation inside the patient's body remote from the at least one first housing.

4. The system of claim 3, wherein said part of the at least one drive unit, such as a drive of the at least one drive unit, is contained in the second housing for advancing and retracting the at least one infusion needle.

5. The system of claim 1, wherein at least a part of the at least one drive unit, such as a drive of the at least one drive unit, is contained in the first housing for advancing and retracting the at least one infusion needle.

6. The system of claim 1, wherein the at least one drive unit comprises a mechanical drive element for transmitting kinetic energy to the at least one infusion needle.

7. The system of claim 6, wherein the mechanical drive element comprises a screw drive connection for advancing and retracting the infusion needle.

8. The system of claim 7, wherein the screw drive connection comprises a threading on the infusion needle engaging a fixedly mounted rack.

9. The system of claim 6, wherein the mechanical drive element comprises at least one rotating shaft directly or indirectly cooperating with the at least one infusion needle so as to cause movement of the infusion needle upon rotation of the rotating shaft, wherein turning the rotating shaft about its axis of rotation causes the infusion needle to advance and/or retract.

10. The system of claim 9, wherein the rotating shaft comprises a screw drive connection, in particular a worm screw.

11. The system of claim 10, wherein the screw drive connection comprises a threading on the infusion needle engaging a fixedly mounted rack.

12. The system of claim 6, wherein the mechanical drive element comprises at least one wire directly or indirectly cooperating with the infusion needle so as to cause movement of the needle upon actuation of the wire, wherein pulling at least one of the at least one wire causes the infusion needle to advance or retract.

13. The system of claim 1, wherein the at least one drive unit comprises a hydraulic drive for transmitting hydraulic energy to the at least one infusion needle for advancing the tip end of the infusion needle, wherein hydraulic fluid of the hydraulic drive is guided through a conduit connecting the at least one infusion needle with the at least one reservoir, and wherein the system is adapted to use as the hydraulic fluid infusion liquid to be injected into the patient's body.

14. The system of claim 13, wherein the system is adapted to use as the hydraulic fluid a secondary liquid different from an infusion liquid to be injected into the patient's body.

15. The system of claim 1, wherein the at least one drive unit comprises as a drive at least one of; at least one electric motor or pump and an electromagnetic drive.

16. The system of claim 15, further comprising wiring for transmitting electric energy from, at least one of; a remote location within the patient's body and the first housing to the second housing, to the at least one of; at least one motor, at least one pump and electromagnetic drive.

17. The system of claim 1, wherein the reservoir comprises at least one first compartment accommodating or adapted to accommodate a first substance and at least one second compartment accommodating or adapted to accommodate a second substance, wherein the implantable system is adapted to cause the two injected substances to be mixed within the body, wherein the substance contained in the at least one second compartment is in at least one of; powder form and freeze-dried form.

18. The system of claim 1, wherein the at least one infusion needle has a tube-like body closed at the tip end and having a laterally arranged delivery exit port.

19. The system of claim 1, further comprising an energy source for providing energy to at least one of the pump, the drive unit and the motor, and any other energy consuming part of the system, wherein the system comprises coupling elements for wireless energy transfer from outside the patient's body to the energy storage means for charging the energy storage means from outside a patient's body, when the energy storage means is implanted in a patient's body, wherein at least one feedback sensor is provided and adapted to sense one or more physical parameters of the patient and/or process parameters of the system, further comprising a feedback subsystem adapted to wirelessly send feedback information relating to the energy to be stored in the energy storage means from inside the human body to the outside thereof, wherein the system is adapted to use the feedback information for adjusting the amount of wireless energy transmitted by the energy transmitter and/or adapted to provide feedback on parameters relevant for the treatment, including the one or more physical parameters of the patient and/or the process parameters of the system.

20. The system of claim 19, wherein the feedback information relates to an energy balance which is defined as the balance between at least one of; an amount of wireless energy received inside the human body and an amount of energy consumed by the at least one energy consuming part, and a rate of wireless energy received inside the human body and a rate of energy consumed by the at least one energy consuming part.

21. The system of claim 1, further comprising a cooling device for preserving the substance by keeping the substance within at least one compartment of the reservoir at a temperature below 37° C.

22. The system of claim 1, comprising an internal control unit and a data transfer port for data transfer between an external data processing device and the internal control unit, wherein the data transfer port is a wireless data transfer port for the data transfer, wherein the internal control unit is programmable.

23. The system of claim 1, comprising an external control unit comprising a wireless remote control to control from outside the patient's body, wherein the external control unit is adapted for at least one of; manual operation by the patient for setting into operation the internal control unit and to program the internal control unit.

24. The system of claim 1, comprising a reservoir with at least one compartment, wherein the reservoir further comprises a gas chamber and an infusion liquid chamber, said chambers being separated by a flexible membrane.

25. The system of claim 1, comprising a reservoir with at least one compartment, wherein the reservoir further comprises an injection port for refilling the reservoir with infusion liquid.

26. The system of claim 1, comprising a reservoir with at least one compartment, wherein the reservoir is adapted to cause a negative pressure in at least one compartment of the reservoir, when drawing infusion liquid from at least one compartment of the reservoir.

27. The system of claim 1, wherein the drive unit is configured to laterally displace the tip end of at least one of said at least one infusion needle in at least two different lateral directions, adapted to displace the infusion needle in at least; a first lateral direction and back, and a second lateral direction and back, wherein the second direction is different from the first direction, and wherein the drive unit further comprises;
 a single, multifunctional drive unit or
 a drive unit including a plurality of different drive units suitably arranged to work in a coordinated fashion, and wherein the drive unit is adapted to displace the infusion needle in the at least two different lateral directions.

* * * * *